United States Patent [19]

Kume et al.

[11] Patent Number: 5,077,401

[45] Date of Patent: Dec. 31, 1991

[54] BENZO-FUSED CYCLIC COMPOUNDS

[75] Inventors: Toyohiko Kume; Toshio Goto; Atsumi Kamochi; Akihiko Yanagi; Shigeki Yagi; Hiroshi Miyauchi; Katsuhiko Shibuya, all of Tokyo, Japan

[73] Assignee: Nihon Tokushu Noyaku Seizo K.K., Tokyo, Japan

[21] Appl. No.: 418,001

[22] Filed: Oct. 6, 1989

Related U.S. Application Data

[62] Division of Ser. No. 209,170, Jun. 17, 1988.

[30] Foreign Application Priority Data

Jun. 22, 1987 [JP] Japan .................. 62-155093
Sep. 17, 1987 [JP] Japan .................. 62-231063
Oct. 15, 1987 [JP] Japan .................. 62-258462

[51] Int. Cl.⁵ ........................................ C07D 279/16
[52] U.S. Cl. .................................... 544/52; 544/50;
544/51; 544/105; 544/236; 546/270; 546/271;
548/125; 548/128; 548/159; 548/221; 71/88;
71/90; 71/92; 71/94; 71/95
[58] Field of Search ............... 71/90, 92, 95, 88, 94;
546/270, 271; 548/128, 125, 159, 221; 544/105,
236, 52, 51, 80

[56] References Cited

U.S. PATENT DOCUMENTS

| | | | |
|---|---|---|---|
| 4,619,687 | 10/1986 | Haga et al. | 71/92 |
| 4,640,707 | 2/1987 | Nagano et al. | 71/96 |
| 4,720,297 | 1/1988 | Haga et al. | 71/90 |
| 4,786,310 | 11/1988 | Haga et al. | 71/90 |
| 4,790,868 | 12/1988 | Nielson | 71/88 |
| 4,792,605 | 12/1988 | Nagano et al. | 544/105 |

OTHER PUBLICATIONS

Haga et al. Chemical Abstracts, vol. 108, 1988, p. 638, 37827z.

*Primary Examiner*—Jose G. Dees
*Assistant Examiner*—Deborah D. Carr
*Attorney, Agent, or Firm*—Sprung Horn Kramer & Woods

[57] ABSTRACT

Herbicidal benzo-fused cyclic compounds of the formula

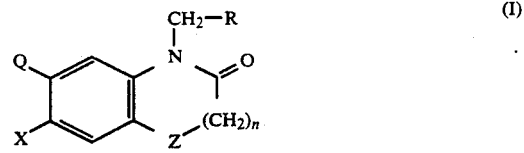

wherein
Q is

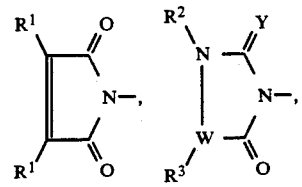

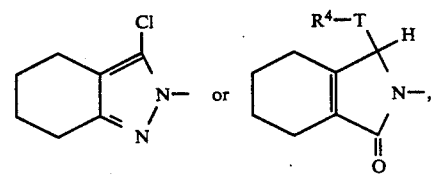

Y is O or S,
W is

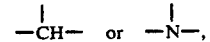

T is O, S, —NH— or

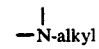

and
R⁴ may represent, together with T, chlorine,
Z is O or S,
X is hydrogen or halogen,
n is 0 or 1 and
R is $C_{3-6}$ *cycloalkyl, and optionally substituted 5-membered heterocyclic group or an optionally substituted 6-membered heteroaromatic group which contains one to three nitrogen atoms,*
and salts thereof.

8 Claims, No Drawings

BENZO-FUSED CYCLIC COMPOUNDS

This is a division of application Ser. No. 209,170, filed June 17, 1988, now allowed.

The present invention relates to novel benzo-fused cyclic compounds, to processes for their preparation and to their use as herbicides.

It has already been disclosed that certain benzoxazine derivatives have herbicidal activities (see EP-OS 170 191).

There have now been found novel benzo-fused cyclic compounds of the formula (I)

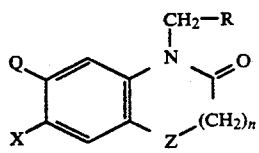

wherein
Q is

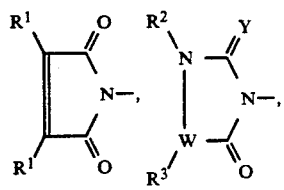

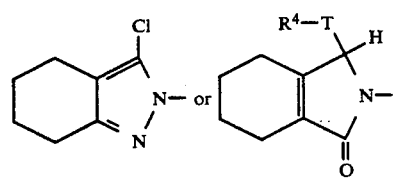

in which
R$^1$ is methyl or one R$^1$ may form tetramethylene, together with another R$^1$,
R$^2$ represents tetramethylene or —CH$_2$CH=CHCH$_2$—, together with R$^3$,
R$^4$ is hydrogen, alkyl, acyl or aryl,
Y is O or S,
W is

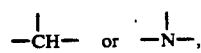

T is O, S, —NH— or

and
R$^4$ may represent, together with T, chlorine,
Z is O or S,
X is hydrogen or halogen,
n is 0 or 1 and
R is C$_{3-6}$ cycloalkyl, an optionally substituted 5-membered heterocyclic group or an optionally substituted 6-membered heteroaromatic group which contains one to three nitrogen atoms, and salts thereof.

The compounds of the formula (I) are obtained by a process in which, a) in the case where Q is

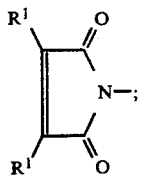

compounds of the formula (II)

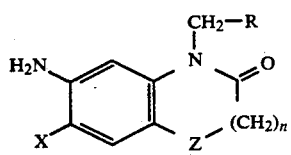

wherein Z, X, R and n have the same meanings as stated above,
are reacted with compounds of the formula (III)

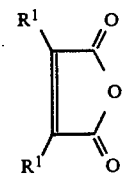

wherein R$^1$ has the same meaning as stated above, in the presence of inert solvents, or
b) in the case where Q is

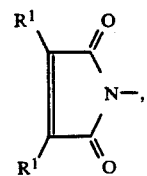

compounds of the formula (IV)

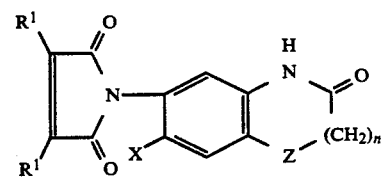

wherein R$^1$, Z, X and n have the same meanings as stated above,
are reacted with compounds of the formula (V)

M—CH$_2$—R  (V)

wherein R has the same meaning as stated above, and M is halogen, methanesulfonyloxy, benzenesulfonyloxy or p-toluenesulfonyloxy,
in the presence of inert solvents and if appropriate in the presence of a base, or
c) in the case where Q is

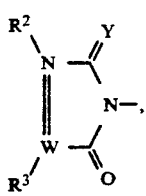

in which
R² represents tetramethylene together with R³, and W is

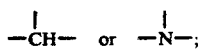

compounds of the formula (VI)

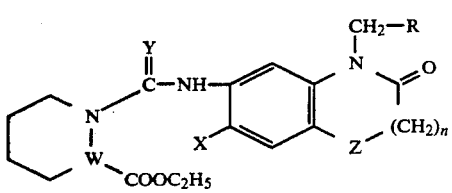
(VI)

wherein Y, W, Z, X, R and n have the same meanings as stated above,
are reacted with appropriate bases in the presence of inert solvents,
or
d) in the case where Q is

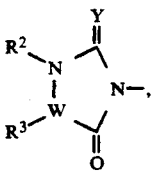

in which
R² represents —CH₂CH=CHCH₂— together with R³, and W is

compounds of the formula (VII)

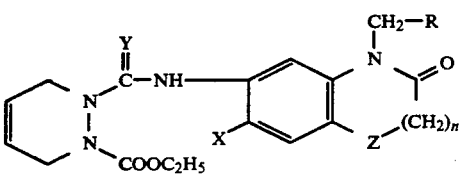
(VII)

wherein Y, Z, X, R and n have the same meanings as stated above,
are reacted with appropriate bases in the presence of inert solvents,
or e) in the case where Q is

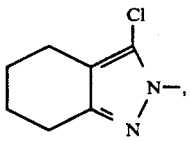

compounds of the formula (VIII)

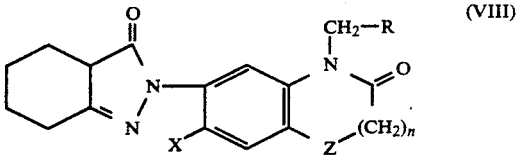
(VIII)

wherein Z, X, R and n have the same meanings as stated above,
are reacted with a chlorinating agent in the presence of inert solvents,
or
f) in the case where Q is

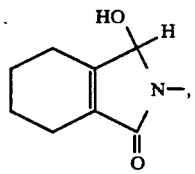

compounds of the formula (Ia)

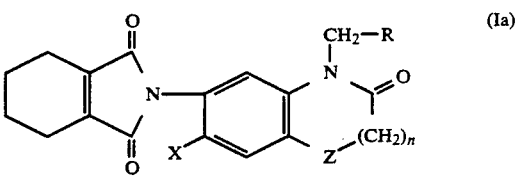
(Ia)

wherein Z, X, R and n have the same meanings as stated above,
are reduced in the presence of inert solvents,
or
g) in the case where Q is

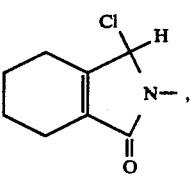

compounds of the formula (Ib)

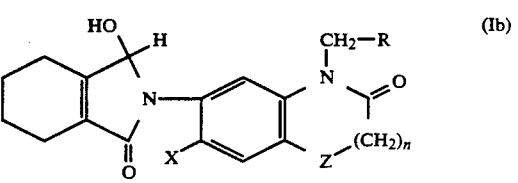
(Ib)

wherein

Z, X, R and n have the same meanings as stated above,
are reacted with a chlorinating agent in the presence of inert solvents, or h) in the case where Q is

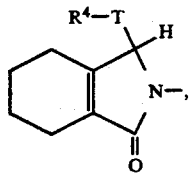

in which
R⁴ is acyl and T is O, then R⁴ is replaced by R⁵; the aforementioned compounds of the formula (Ib)

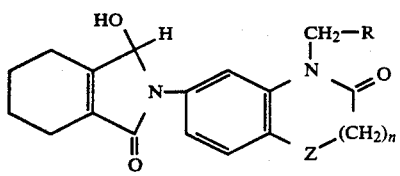

wherein
Z, X, R and n have the same meanings as stated above,
are reacted with compounds of the formula (IX)

R⁵—Cl     (IX)

wherein R⁵ is acyl,
or
with compounds of the formula (X)

(R⁵)₂O     (X)

wherein R⁵ has the same meaning as stated above, in the presence of inert solvents, and, if appropriate, in the presence of bases, or i) in the case where Q is

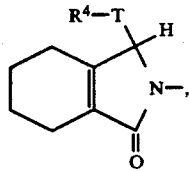

provided that R⁴—T— does not represent —OH, —Cl or acyloxy, then R⁴—T— is replaced by R⁶; compounds of the formula (Ic)

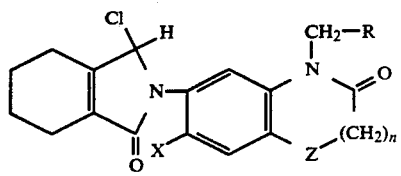

wherein

Z, X, R and n have the same meanings as stated above,
are reacted with compounds of the formula (XI)

R⁶—H     (XI)

wherein R⁶ is alkoxy, alkylthio, phenoxy, phenylthio, alkylamino or dialkylamino, in the presence of inert solvents and if appropriate in the presence of a base.

The benzo-fused cyclic compounds according to the invention exhibit powerful herbicidal properties.

Surprisingly, the benzo-fused cyclic compounds according to the invention exhibit not only a substantially greater herbicidal action than those known for the aforesaid prior art, but also a favorable compatibility with crops, namely without phytotoxicity. In particular, the benzo-fused cyclic compounds can precisely and effectively control upland weeds by pre-emergence treatment thereof.

Among the benzo-fused compounds of the formula (I) according to the invention preferred compounds are those in which Q is

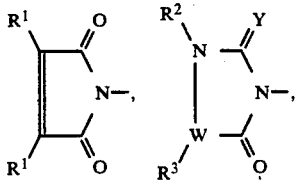

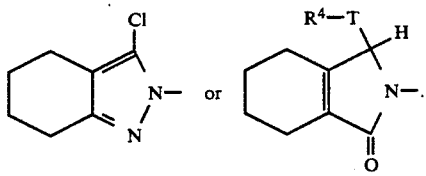

R¹ is methyl or one R¹ may form tetramethylene, together with another R¹,
R² represents tetramethylene or —CH₂—CH=CHCH₂—, together with R³,
R⁴ is hydrogen, C₁-C₄-alkyl, C₁-C₄-alkylcarbonyl or phenyl,
Y is O or S,
W is

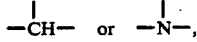

T is O, S, —NH— or

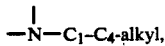

and
R⁴ may represent, together with T, chlorine,
Z is O or S,
X is hydrogen or halogen,
n is 0 or 1 and
R is C₃₋₆ cycloalkyl, an optionally substituted 5-membered heterocyclic group which contains one to three nitrogen atoms or one or two nitrogen atoms together with an oxygen or a sulfur atom, or an optionally substituted 6-membered heteroaromatic group which contains one to three nitrogen atoms, identical or different substituents in each case being: amino, C₁-C₄-alkylamino, Di(C₁-C₄-alkyl)amino, formylamino, C₁-C₄-alkylcarbonylamino, halogen, C₁-C₄-alkoxy, C₁-C₄-alkylthio, C₁-C₄-alkyl, halogeno-C₁-C₄-alkyl and/or C₁-C₄-alkoxy-C₁-C₄-alkyl; and in case R is a 6-membered heteroaromatic group, also their hydrochloride salts.

Among the benzo-fused cyclic compounds according to the invention, of the formula (I), particularly preferred compounds are those in which Q is

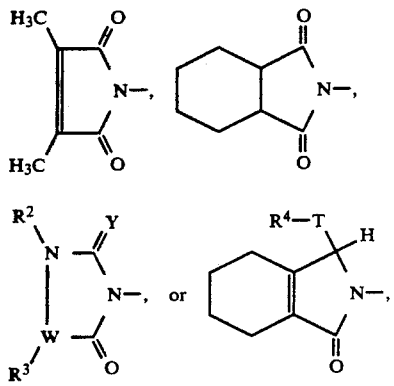

in which
R² represents tetramethylene or —CH₂CH=CHCH₂—, together with R³,
R⁴ is hydrogen, methyl, ethyl, methylcarbonyl or phenyl,
T is oxygen or sulfur, or R⁴ may represent, together with T, chlorine,
Y is O or S,
W is

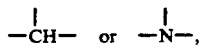

Z is O or S,
X is hydrogen or fluorine,
R is cyclopropyl, an optionally substituted 5-membered heterocyclic group which contains at least one nitrogen atom, and either an oxygen atom or a sulfur atom or a 6-membered heteroaromatic group which contains one or two nitrogen atoms,
identical or different substituents being in each case amino, methylamino, ethylamino, dimethylamino, formylamino, acetamido, fluoro, chloro, bromo, methoxy, ethoxy, methylthio, ethylthio, methyl, ethyl, isopropyl, trichloromethyl, trifluoromethyl and/or methoxymethyl, and n is 0 or 1, Very particularly preferred benzo-fused cyclic compounds of the formula (I) are those in which Q is

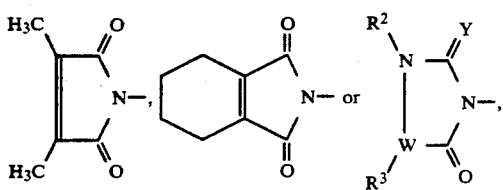

in which
R² represents tetramethylene or —CH₂CH=CHCH₂— together with R³,
Y is O or S,
W is

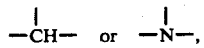

Z is O or S,
X is fluorine,
n is 0 or 1 and
R is an optionally substituted heterocyclic group comprising the following systems: tetrahydrofuran, furan, thiophene, pyrazole, imidazole, 1,2,4-triazole, tetrazole, isoxazole, oxazole, 1,2,4-oxadiazole, 1,2,5-oxadiazole, 1,3,4-oxadiazole, isothiazole, thiazole, 1,2,3-thiadiazole, 1,2,4-thiadiazole, 1,2,5-thiadiazole, 1,3,4-thiadiazole, pyridine, pyrimidine and pyrazine, identical or different substituents being in each case amino, methylamino, ethylamino, dimethylamino, formylamino, acetamido, fluoro, chloro, bromo, methoxy, ethoxy, methylthio, ethylthio, methyl, ethyl, isopropyl, trichloromethyl, trifluoromethyl and/or methoxymethyl.

In the formula (I), as particularly preferred examples of R, there can be mentioned each group based on the following heterocyclic systems: tetrahydrofuran, furan, thiophene, pyrazole, imidazole, 1,2,4-triazole, tetrazole, isoxazole, oxazole, 1,2,4-oxadiazole, 1,2,5-oxadiazole, 1,3,4-oxadiazole, isothiazole, thiazole, 1,2,3-thiadiazole, 1,2,4-thiadiazole, 1,2,5-thiadiazole, 1,3,4-thiadiazole, pyridine, pyrimidine and pyrazine.

The above heterocyclic groups may be optionally substituted by at least one substituent selected from amino, methylamino, ethylamino, dimethylamino, formylamino, acetamido, fluoro, chloro, bromo, methoxy, ethoxy, methylthio, ethylthio, methyl, ethyl, isopropyl, trichloromethyl, trifluoromethyl and methoxymethyl.

Specifically, the following compounds may be mentioned:
6-fluoro-3-(pyridin-2-ylmethyl)-5-(3,4-dimethyl-2,5-dioxo-2,5-dihydropyrrol-1-yl)-2(3H)-benzothiazolone,
4-(pyridin-2-ylmethyl)-6-(4,5,6,7-tetrahydro-2H-isoindole-1,3-dion-2-yl)-2H-1,4-benzoxazin-3(4H)-one,
7-fluoro-4-(pyridin-2-ylmethyl)-6-(4,5,6,7-tetrahydro-2H-isoindole-1,3-dion-2-yl)-2H-1,4-benzoxazin-3(4H)-one,
7-fluoro-4-(pyrazin-2-ylmethyl)-6-(4,5,6,7-tetrahydro-2H-isoindole-1,3-dion-2-yl)-2H-1,4-benzoxazin-3(4H)-one,
6-fluoro-3-(isoxazol-3-ylmethyl)-5-(4,5,6,7-tetrahydro-2H-isoindole-1,3-dion-2-yl)-2(3H)-benzoxazolone,
6-fluoro-3-(5-methyl-1,2,4-oxadiazol-3-ylmethyl)-5-(4,5,6,7-tetrahydro-2H-isoindole-1,3-dion-2-yl)-2(3H)-benzoxazolone,
6-fluoro-3-(isoxazol-3-ylmethyl)-5-(4,5,6,7-tetrahydro-2H-isoindole-1,3-dion-2yl)-2(3H)-benzothiazolone,
6-fluoro-3-(5-methylisoxazol-3-ylmethyl)-5-(4,5,6,7-tetrahydro-2H-isoindole-1,3-dion-2-yl)-2(3H)-benzothiazolone,
6-fluoro-3-(5-methyl-1,2,4-oxadiazol-3-ylmethyl)-5-(4,5,6,7-tetrahydro-2H-isoindole-1,3-dion-2-yl)-2(3H)-benzothiazolone, 6-fluoro-3-(5-methyl-1,2,4-oxadiazol-3-ylmethyl)-5-(1,2-tetramethylene-1,2,4-triazolidine-3,5-dion-4-yl)-2(3H)-benzothiazolone, 6-fluoro-3-(isoxazol-3-ylmethyl)-5-(1,2-tetramethylene-1,2,4-triazolidine-3,5-dion-4-yl)-2(3H)-benzothiazolone, 6-fluoro-3-(5-methyl-1,2,4-oxadiazol-3-ylmethyl)-5-(1,2-tetramethylene-1,2,4-triazolidin-3-one-5-thion-4-yl)-2(3H)-benzothiazolone, 6-fluoro-3-(isoxazol-3-ylmethyl)-5-(1,2-tetramethylene-1,2,4-triazolidin-3-one-5-thion-4-yl)-2(3H)-benzothiazolone, 4-(isoxazol-3ylmethyl)-6-(3,4-dimethyl-2,5-dihydropyrrole-2,5-dion-1-yl)-2H-1,4-benzoxazin-3(4H)-one, 6-(3,4-dimethyl-2,5-dihydropyrrole-2,5-dion-1-yl)-4-(5-methyl-1,2,4-oxadiazol-3-ylmethyl)-2H-1,4-benzoxazin-3(4H)-one, 4-(isoxazol-3-ylmethyl)-6-(4,5,6,7-tetrahydro-2H-isoindole-1,3-dion-2-yl)-2H-1,4-benzoxazin-3(4H)-one, and 4-(5-methyl-1,2,4-oxadiazol-3-ylmethyl)-6-(4,5,6,7-tetrahydro-2H-isoindole-1,3-dion-2-yl)-2H-1,4-benzoxazin-3(4H)-one.

If, for example, in the above process a), 6-amino-7-fluoro-4-(pyridin-2-ylmethyl)-2H-1,4-oxazin-3(4H)-one and 2,3-dimethylmaleic anhydride are used as starting materials, the course of the reaction can be represented by the following equation:

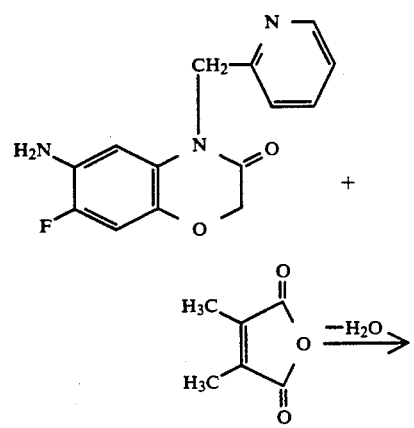

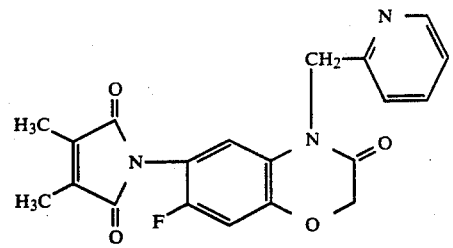

If, for example, in the above process b), 7-fluoro-6-(4,5,6,7-tetrahydro-2H-isoindole-1,3-dion-2-yl)-2H-1,4-benzoxazin-3(4H)-one and 2-chloromethylpyridine are used as starting materials, the course of the reaction can be represented by the following equation:

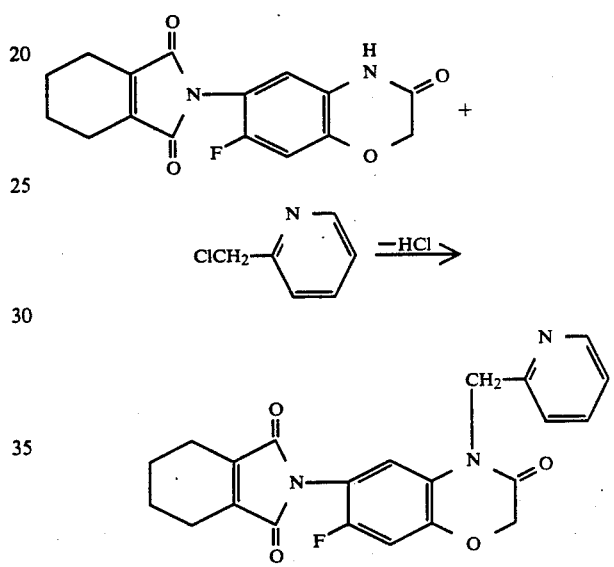

If, for example, in the above process c), 5-(2-ethoxycarbonyl-hexahydropyridazin-1-ylcarbonylamino)-6-fluoro-3-(5-methyl-1,2,4-oxadiazol-3-ylmethyl)-2(3H)-benzothiazolone and sodium ethoxide are used as starting materials, the course of the reaction can be represented by the following equation:

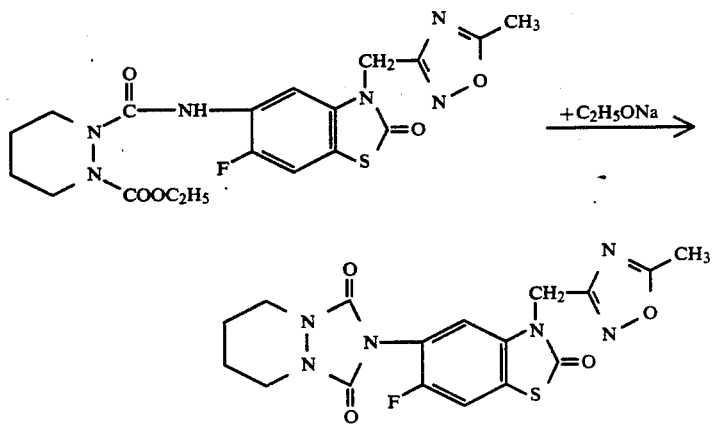

If, for example, in the above process d) 6-(2-ethoxycarbonyl-1,2,3,6-tetrahydropyridazin-1-ylcarbonylamino)-7-fluoro-4-(pyridin-2-ylmethyl)-2H-1,4- benzoxazin-3(4H)-one and sodium ethoxide are used as starting materials, the course of the reaction can be represented by the following equation:

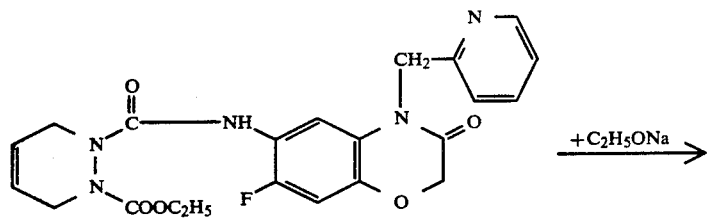

If, for example, in the above process e), 6-fluoro-5-(3,3a,4,5,6,7-hexahydro-2H-indazol-3-on-2-yl)-3-(isoxazol-3-ylmethyl)-2(3H)-benzothiazolone and phosphoryl chloride are used as starting materials, the course of the reaction can be represented by the following equation:

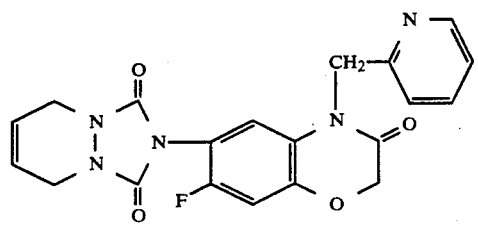

If, for example, in the above process f), 7-fluoro-4-(pyridin-2-ylmethyl)-6-(4,5,6,7-tetrahydro-2H-isoindole-1,3-dion-2-yl)-2H-1,4-benzoxazin-3(4H)-one and sodium boron hydride are used as starting materials, the course of the reaction can be represented by the following equation:

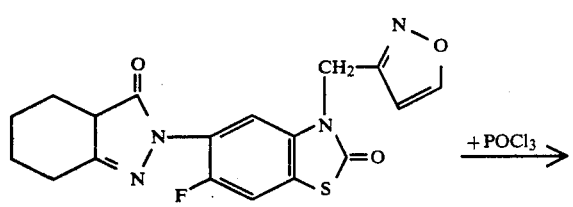

If, for example, in the above process g), 7-fluoro-4-(pyridin-2-ylmethyl)-6-(3-hydroxy-4,5,6,7-tetrahydroisoindolin-1-on-2-yl)-2H-1,4-benzoxazin-3(4H)-one and thionyl chloride are used as starting materials, the course of the reaction can be represented by the following equation:

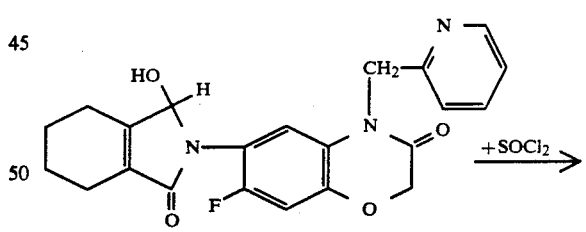

If, for example, in the above process h), 7-fluoro-4-(pyridin-2-ylmethyl)-6-(3-hydroxy-4,5,6,7-tetrahydroisoindolin-1-on-2-yl)-2H-1,4-benzoxazin-3(4H)-one and acetic anhydride are used as starting materials, the course of the reaction can be represented by the following equation:

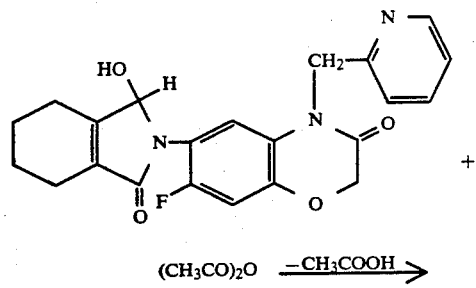

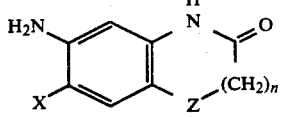

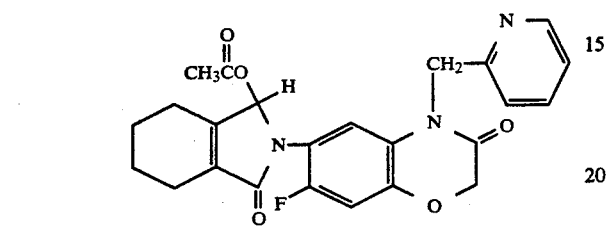

If, for example, in the above process i), 6-(3-chloro-4,5,6,7-tetrahydroisoindolin-1-on-2-yl)-7-fluoro-4-(pyridin-2ylmethyl)-2H-1,4-benzoxazin-3(4H)-one and ethanol are used as starting materials, the course of the reaction can be represented by the following equation:

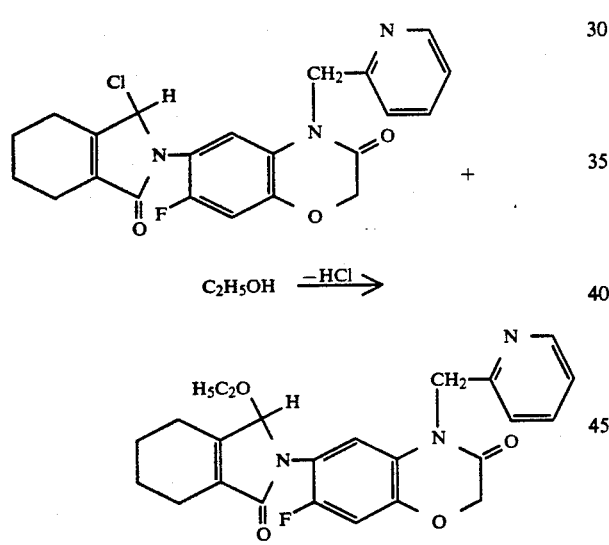

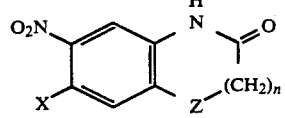

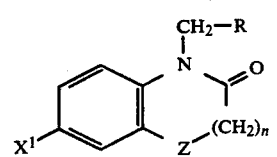

Formula (II) provides a definition of the compounds required as starting materials in the process a) according to the invention.

According to the formula (II), Z, X, R and n preferably have the same meanings as already given above.

The compounds of the formula (II) are novel, and in general can be obtained by a process in which j) compounds of the formula (XII)

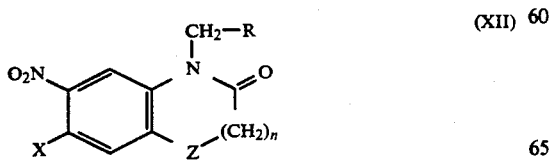

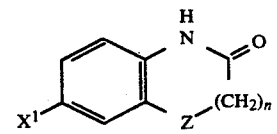

wherein Z, X, R and n have the same meanings as stated above, are reduced in the presence of inert solvents,
or
k) compounds of the formula (XIII)

(XIII)

wherein Z, X and n have the same meanings as stated above, are reacted with the aforementioned compounds of the formula (V)

M—CH₂—R in the presence of inert solvents and if appropriate in the presence of a base.

The compounds of the formula (XII), in the process j), are novel and for instance can be obtained by a process in which l) compounds of the formula (XIV)

(XIV)

wherein Z, X and n have the same meanings as stated above, are reacted with the aforementioned compounds of the formula (V) in the presence of inert solvents and if appropriate in the presence of a base, or m) in the formula (XII), in the case where X is halogen; compounds of the formula (XV)

(XV)

wherein Z, R and n have the same meanings as stated above and X¹ is halogen, are nitrated, if appropriate, in the presence of inert solvents and, if appropriate, in the presence of a catalyst.

The compounds of the formula (XV), in the process m), are novel and for instance can be obtained by a process in which n) compounds of the formula (XVI)

(XVI)

wherein Z, X¹ and n have the same meanings as stated above, are reacted with the aforementioned compounds of the formula (V) in the presence of inert solvents and if appropriate in the presence of a base.

Alternatively, in the formula (XV), said compounds of the case where $X^1$ is fluorine may be obtained from 4-position substituted derivatives of 7-amino-2H-1,4-benzoxazin-3(4H)-one according to the Schiemann reaction (see Organic Reactions V p. 193).

The above 4-position substituted derivatives of 7-amino-2H-1,4-benzoxazin-3(4H)-one can be prepared by reducing products which can be obtained by reacting 7-nitro-2H-1,4-benzoxazin-3(4H)-one with the aforementioned compounds of the formula (V).

The above 7-nitro-2H-1,4-benzoxazin-3(4H)-one is known (see J. Chem. Soc., 1928, 3046 or Synthesis, 1982, 986).

The compounds of the formula (XVI), in the process n), are known (see Chem. Abst., vol. 53, p. 5246, EP-OS 170,191 or Farmco Ed. Sci., vol. 32, No. 5, p. 348).

In the formula (XVI), said compounds of the case where Z is S and n is O can be easily obtained by hydrolyzing a known 2-chloro-6-halogenobenzothiazole with concentrated hydrochloric acid in ethanol.

The compounds of the formula (XIV), in the process l), are known (see Japanese Patent Laid-open 125529/1974, ibid 132872/1987, EP-OS 170191, GDR Patent 615131)

The compounds of the formula (XIII), in the process k), are known compounds (see J. Am. Chem. Soc. vol. 80, p. 1662, EP-OS 170191, Chem. Abst., vol. 51, 17926 f, Japanese Patent Laid-open 155267/1987).

In carrying out the above process j), stannous chloride and hydrochloric acid can be used for the reduction.

In carrying out the above process k), as inert solvents, there may be exemplified:

water, alcohols, ketones, nitriles, tetrahydrofuran, dioxane, dimethylformamide, dimethylsulfoxide and the like.

The process k) may be carried out in the presence of a base, such as sodium hydroxide, potassium hydroxide potassium carbonate and the like.

The process k) can be carried out at temperatures between about 0° and about 150° C., preferably between about 30° and about 100° C.

In carrying out the process l), as inert solvents, there may be exemplified the same those as in the process k).

The process l) can also be carried out in the presence of a base which is the same as exemplified in the process k).

The process l) can be carried out at temperatures between about 20° and about 180° C., preferably between about 30° and about 100° C.

The process m) can be carried out in accordance with a conventional nitration method.

Possible diluents for carrying out the preparation process m) are all the solvents which can usually be employed for such nitration reactions. The nitric acid simultaneously employed as a reagent or a mixture thereof with catalyst acids, such as, for example, sulfuric acid, is preferably used in a corresponding excess as the diluent.

If appropriate, inert organic solvents, such as for example, glacial acetic acid or chlorinated hydrocarbons, such as methylene chloride, chloroform or carbon tetrachloride, can also be used as diluents.

Possible catalysts or reaction auxiliaries for carrying out the preparation process are likewise the catalysts which are customary for such nitration reactions, such as, for example, sulfuric acid, iron-III chloride or other Lewis acids or acetic anhydride.

The reaction temperatures can be varied within a substantial range in carrying out the preparation process. In general, the reaction is carried out between $-50°$ C. and $+200°$ C., preferably between $-20°$ C. and $+50°$ C.

For carrying out process m) the mol ratio of nitrating agent to the compounds of the formula (XV) is 0.98 to 1.5, preferably 1 to 1.2.

The process n) can be carried out in the same way as in the above process l), and the reaction temperature therefor is between about 0° and about 150° C., preferably about 30° and about 100° C.

The compounds of the formula (III) in the process a) are known, and as examples there may be mentioned:
2,3-dimethylmaleic anhydride and
3,4,5,6-tetrahydrophthalic anhydride.

Formula (IV) provides a definition of the compounds required as starting materials in the process b) according to the invention.

According to the formula (IV), $R^1$, Z, X and n preferably have the same meanings as have already been given above.

The compounds of the formula (IV) include in part known compounds (see EP-OS 170 191, Japanese Patent Laid-open 155 276/1987), and in general can be obtained by a process in which o) the aforementioned compounds of the formula (XIII) are reacted with the aforementioned compounds of the formula (III) in the presence of inert solvents.

The above process l) can be carried out in accordance with a method described in Agr. Biol. Chem., vol. 40, No. 4, p. 745 or Pestic. Biochem. Physiol., vol. 14, pp 153–160.

Formula (V) provides a definition of the compounds required as starting materials in the process b) according to the invention.

According to the formula (V), R preferably has the same meanings as already given above, and M preferably means chlorine, bromine, iodine, methanesulfonyloxy, benzenesulfonyloxy or p-toluenesulfonyloxy. M especially means chlorine.

The compounds of the formula (V) are known as alkylating agents in organic chemistry.

In the case, of the formula (V), where R is a 5-membered heterocyclic group, there may be mentioned as specific examples:
3-(chloromethyl)isoxazole,
3-chloromethyl-5-methylisoxazole,
3-chloromethyl-1-methyl-1,2,4-triazole,
3-chloromethyl-5-methyl-1,2,4-oxazole,
5-chloromethyl-3-methyl-1,2,4-oxazole,
4-(chloromethyl)thiazole,
4-chloromethyl-2-methylthiazole,
3-chloromethyl-4-methyl-1,2,5-oxadiazole, and
3-bromomethyl-1,2,5-thiadiazole.

In the case, of the formula (V), where R is a 6-membered heteroaromatic group, there may be mentioned as specific examples:
2-(chloromethyl)pyridine,
2-(chloromethyl)pyrazine,
2-(chloromethyl)pyrimidine,
4-(chloromethyl)pyrimidine,
2-chloromethyl-1,3,5-triazine, and
3-(chloromethyl)pyridazine.

Specifically, 2-(chloromethyl)pyridine exemplified above can be obtained by chlorinating 2-picoline with N-chlorosuccinimide according to a conventional method, or by chlorinating 2-(hydroxymethyl)pyridine with thionyl chloride according to a method described in J. Pharm. Soc. Japn., vol. 79, p. 1277. The above 2-(hydroxymethyl)pyridine can be obtained by hydrolyzing the product which is made by reacting 2-methypyridine N-oxide with acetic anhydride (see J. Am. Chem. Soc., vol. 76, p. 1286 and Pharm. Bull., vol. 3, p. 413).

Formula (VI) provides a definition of the compounds required as starting materials in the process c) according to the invention.

According to the formula (VI), Y, W, Z, X, R and n preferably have the same meanings as already given above.

The compounds of the formula (VI) are novel, and in general can be obtained by a process in which
p) compounds of the formula (XVII)

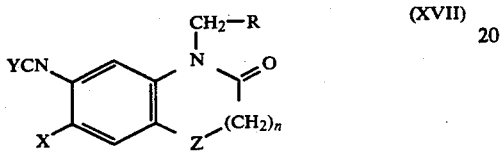

wherein Y, Z, X, R and n have the same meanings as stated above,
are reacted with ethyl pipecolinate or 1-ethoxycarbonylhexahydropyridazine in the presence of inert solvents.

The compounds of the formula (XVII), in the process p), are novel, and in general, can be obtained by a process in which q) the aforementioned compounds of the formula (II) are reacted with phosgene or thiophosgene in the presence of inert solvents.

The process q) can be carried out, in the case where Y is O, in accordance with a method described in J. Am. Chem. Soc., vol. 72, p. 1888 or Org. Synthesis, vol. 2, p. 453, and in the case where Y is S, in accordance with a method described in J. Org. Chem., 1953, p. 1092 or J. Chem. Soc., 1927, p. 1186, respectively.

Ethyl pipecolinate, in the process m), is a commercially known compound, and 1-ethoxycarbonylhexahydropyridazine can be easily obtained by a method described in Bull. Soc. Chim. France, 1957, p. 704 or U.S. Pat. No. 2,841,584.

Appropriate bases in the process c) include alkoxides such as sodium ethoxide, sodium methoxide; alkali metal hydroxides such as potassium hydroxide, sodium hydroxide; triethylamine and the like.

Formula (VII) provides a definition of the compounds required as starting materials in the process d) according to the invention.

According to the formula (VII), Y, Z, X, R and n preferably have the same meanings as have already been mentioned as preferred therefor in connection with the description of the compounds of the formula (I) according to the invention.

The compounds of the formula (VII) are novel, and in general, can be obtained by a process in which r) the aforementioned compounds of the formula (XVII) are reacted with 1-ethoxycarbonyl-1,2,3,6-tetrahydropyridazine in the presence of inert solvents.

1-ethoxycarbonyl-1,2,3,6-tetrahydropyridazine can be obtained by a method described in Bull. Soc. Chim. France, 1957, p. 704 or U.S. Pat. No. 2,841,584.

The above processes p) and q) can be carried out, in accordance with a method described in Agr. Biol. Chem., vol. 40, No. 4, p. 745.

Appropriate bases in the process d) include the same as exemplified in the process c).

Formula (VIII) provides a definition of the compounds required as starting materials in the process e) according to the invention.

According to the formula (VIII), Z, X, R and n preferably have the same meanings as already given above.

The compounds of the formula (VIII) are novel, and in general can be obtained by a process in which
s) compounds of the formula (XVIII)

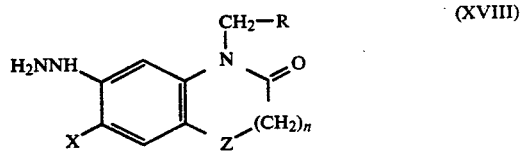

wherein Z, X, R and n have the same meanings as stated above,
are reacted with 2-ethoxycarbonylcyclohexanone in the presence of inert solvents and if appropriate in the presence of a base.

The compounds of the formula (XVIII), in the process s) are novel and can be obtained by a process in which t) the aforementioned compounds of the formula (II) are diazotizated in hydrochloric acid, and successively reduced.

2-ethoxycarbonylcyclohexanone is a commercial product.

In carrying out the above process s), as inert solvents, there may be exemplified:
alcohols such as ethanol; isopropanol; methyl cellosolve, dioxane, toluene, xylene and the like.

The process s) may be carried out in the presence of a base, for example sodium methoxide, sodium ethoxide, triethylamine and the like.

The process s) can be carried out at temperatures between about 20 and about 150° C., preferably between about 50 and about 100° C.

The above process t) can be carried out, in accordance with a method described in "Methoden der Organischen Chemie", vol. 2, p. 177.

As a chlorinating agent in the process e), there may be mentioned: phosgene, thionyl chloride, phosphoryl chloride, oxalyl chloride, and trichloromethyl chloroformate.

Formula (Ia) provides a definition of the compounds required as starting materials in the process f) according to the invention.

Formula (Ib) provides a definition of the compounds required as starting materials in the processes g) and h) according to the invention.

Formula (Ic) provides a definition of the compounds required as starting materials in the process i) according to the invention.

The formula (Ia), (Ib) and (Ic) are a part of the compounds of the formula (I) according to the invention.

A chlorinating agent in the process g) is the same as already exemplified in the proces e).

Formulae (IX) or (X) provide a definition of the compounds required as starting materials in the process h) according to the invention.

The compounds of the formulae (IX) or (X) are known acylating agents, and as examples, there may be mentioned: acetyl chloride, acetic anhydride, and propionyl chloride.

Formula (XI) provides a definition of the compounds required as starting materials in the process i) according to the invention.

The compounds of the formula (XI) are known, $R^6$ preferably meaning $C_1$–$C_4$-alkylthio, phenoxy, phenylthio, $C_1$–$C_4$-alkylamino or di-$C_1$–$C_4$-alkylamino.

As examples, there may be mentioned in particular: Methanol, ethanol, phenol, ethanethiol, benzenethiol, methylamine, dimethylamine and isopropylamine.

The compounds of the formulae (II), (XII), (XV), (XVII) and (XVIII) are novel and may be represented by the following formula (XIX)

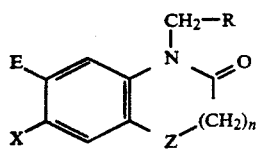

(XIX)

wherein E is hydrogen, nitro, amino, hydrazino, cyanato or thiocyanato,
X is hydrogen or halogen,
Z is O or S,
R is $C_{3-6}$ cycloalkyl, an optionally substituted 5-membered heterocyclic group or an optionally substituted 6-membered heteroaromatic group which contains one to three nitrogen atoms, and
n is 0 or 1.

In formula (XIX) R has the preferred, particularly preferred and very particularly preferred definitions which have already been mentioned describing the compounds of formula (I).

Suitable diluents in the process a) according to the invention are all inert solvents. Those preferentially include organic acids such as acetic acid, propionic acid and the like.

The process a) can be carried out in accordance with a method described in Agr. Biol. Chem., vol. 40, p. 745 hereinabove, and practically the desired compounds can be obtained by refluxing the two starting materials of the formulae (II) and (III) in acetic acid.

For carrying out process a) the mol ratio of the compounds of the formula (II) to the compounds of the formula (III) is 0,8 to 1,0, preferably 0,9 to 0,99.

The reaction temperature can be varied within a relatively wide range in carrying out the process a). In general, the reaction is carried out at temperatures between 60° and 150° C., preferably between 90° and 120° C.

In carrying out the process b), suitable diluents preferably include water, nitriles such as acetonitrile, alcohols such as ethanol, acid amides such as N,N-dimethylformamide, sulfoxides such as dimethylsulfoxide, ketones such as acetone, ethers such as tetrahydrofuran, dioxane and ethyleneglycoldimethylether and the like.

The process b) can also be carried out in the presence of a base and as examples of bases these preferably include sodium carbonate, potassium carbonate, sodium hydride, potassium hydroxide, sodium hydroxide, sodium methoxide, sodium ethoxide, potassium tert.-butoxide and the like.

The reaction temperature of the process b) can be varied within a substantial range. In general, the reaction is carried out at temperatures between about 20° and about 150° C., preferably between about 30° and about 100° C.

The reaction of the process b) can be carried out under normal, elevated or reduced pressure.

In carrying out the process b) there are employed, per mol of the compounds of the formula (IV), 1 to about 1.2 mols of the compounds of the formula (V) in the presence of an inert solvent and a base.

In carrying out the processes c) and d), suitable diluents preferentially include alcohols such as ethanol; isopropanol; tert.-butanol; methyl cellosolve (ethyleneglycolmonomethyl ether), dioxane, N,N-dimethylformamide, dimethylsufoxide, sulfolane and the like.

The process c) and d) can be carried out at temperatures between about 50° and about 130° C., preferably between about 70° and about 90° C.

The processes c) and d) can be carried out, in accordance with a method described in Agr. Biol. Chem., vol. 40, No. 4, p. 745, and for instance, in carrying out the process c) there are employed, per mol of the compounds of the formua (VI), 0.01 to 0.5 mol of sodium ethoxide at reaction temperature as set up above, during 0.5 to 16 hours, in the presence of inert solvents as exemplified above, and in carrying out the process d), in place of the compounds of the formula (VI), the compounds of the formula (VII) are employed under the same reaction condition as the above performance of the process c).

In practice, the aimed compounds of the formula (I) by the process c) can also be preferably obtained by conducting successively the processes q) and c) without isolating the compounds of the formula (VI).

In practice, the aimed compounds of the formula (I) by the process d) can also be preferably obtained by conducting successively the processes r) and d) without isolating the compounds of the formula (VII).

In carrying out the process e), suitable diluents preferentially include toluene, xylene, benzene and the like.

The process e) can be carried out at temperatures between about 20° and about 150° C., preferably between about 50° and about 130° C.

For carrying out process e) the mol ratio of chlorinating agent to the compounds of the formula (VIII) is 1 to 3, preferably 1 to 1,5.

The process e) can be carried out, in accordance with a method described in Japanese Patent Laid-open 30761/1987.

The aimed compounds of the formula (I) by the process e) can also be obtained by conducting successively the processes s) and e) without isolating the compounds of the formula (VIII).

In carrying out the process f), suitable diluents preferably include water, alcohols such as ethanol and the like, and reducing agents preferably include alkali metal hydride such as sodium boron hydride, aluminum boron hydride, and the like.

The process f) can be carried out at temperatures between about −10° and about 80° C., preferably about 0° and about 50° C.

For carrying out process f) the amount of a reducing agent is that equivalent to at least 2 mols, preferably 2,2 to 4 mols, of hydrogen per mol of the compounds of the formula (Ia).

In carrying out the process g), suitable diluents preferably include dichloromethane, chloroform and the like, and as a chlorinating agent, thionyl chloride can be exemplified.

The process g) can be carried out at temperatures between about 30° and about 70° C., preferably between about 30° and about 50° C.

The process g) can be carried out at temperatures between about 0° and about 80° C.

For carrying out process g) the mol ratio of clorinating agent to the compounds of the formula (Ib) is 1 to 2, preferably 1.05 to 1.5.

In carrying out the process h), suitable diluents preferably include benzene, xylene, toluene, tetrahydrofuran and the like.

The process h) may also be carried out in the presence of a base and as example, these preferably include pyridine, 4-(dimethylamino)pyridine, triethylamine, dimethylaniline and the like.

For carrying out process h) the mol ratio of the compounds of the formula (IX) to the compounds of the formula (Ib) is 0.9 to 1.2, preferably 1 to 1.1.

In carrying out the process i), suitable diluents preferably include alcohols such as ethanol; ketones such as acetone and methylethylketone; ethers such as tetrahydrofuran, nitriles such as acetonitrile; aromatic hydrocarbons such as benzene, toluene, xylene and the like.

The process i) may be carried out in the presence of a base and as example, these include the same those as exemplified in the process h).

The process i) can be carried out at temperatures between about 0° and about 100° C.

For carrying out process i) the mol ratio of the compounds of the formula (XI) to the compounds of the formula (Ic) is 0.98 to 1.5, preferably 1 to 1.2.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example aforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted into the customary formulations, such as solutions, emulsions, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquified gaseos or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixes being possible.

Mixtures with other known active compounds, such as herbicides, fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing. They are used, in particular, after emergence of the plants.

The amount of active compound used can vary within a substantial range. It depends essentially on the nature of the desired effect. In general, the amounts used are between about 0.0005 and about 3 kg of active compound per hectare of soil surface, preferably between about 0.001 and about 2 kg per ha.

The preparation and the use of the active compounds according to the invention are illustrated by the following examples. It should be noted that the scope of the invention is not limited only to the technical contents of the examples.

PREPARATIVE EXAMPLES

EXAMPLE 1

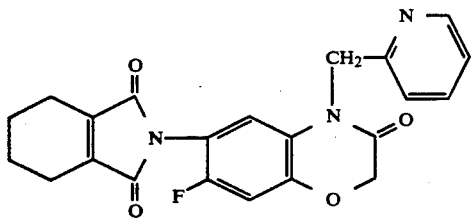

A mixture of 6-amino-7-fluoro-4-(pyridin-2-ylmethyl)-2H-1,4-benzoxazin-3(4H)-one (2 g), 3,4,5,6-tetrahydrophthalic anhydride (1.2 g) and acetic acid (50 ml) was heated under reflux for 1 hour. The acetic acid was distilled off under a reduced pressure, and the residue was dissolved in toluene (100 ml), washed in a saturated aqueous solution of sodium bicarbonate and then in water, and dried over anhydrous sodium sulfate. The toluene was distilled off under a reduced pressure, and the resultant residue was recrystallized from ethanol, whereby the aimed product, namely, 7-fluoro-4-(pyridin-2-ylmethyl)-6-(4,5,6,7-tetrahydro-2H-isoindole-1,3-dion-2-yl)-2H-1,4-benzoxazin-3(4H)-one (2.4 g) was obtained. m.p. 188°–190° C.

In the same way as shown in Example 1, it is possible to prepare 6-(3,4-dimethyl-2,5-dioxo-2,5-dihydropyrrol-1-yl)-7-fluoro-4-(pyridin-2-ylmethyl)-2H-1,4-benzoxazin-3(4H)-one.

EXAMPLE 2

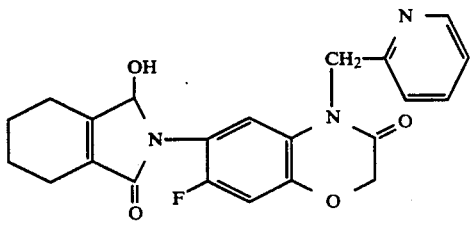

The compound (6.9 g) obtained in Example 1 was dissolved in methanol (200 ml). To this solution was portionwise added sodium borohydride (0.7 g) at a temperature of 20° to 30° C. The reaction mixture was stirred at room temperature for 30 minutes, poured into ice water (600 ml), and extracted with ethyl acetate (250 ml). The extract was washed with water, dried over sodium sulfate anhydride, and distilled to remove the solvent therefrom, so that the aimed product i.e. 7-fluoro-4-(pyridin-2-ylmethyl)-6-(3-hydroxy-4,5,6,7-tetrahydroisoindolin-1-on-2-yl)-2H-1,4-benzoxazin-3(4H)-one (6.9 g) was obtained as an amorphous material.

EXAMPLE 3

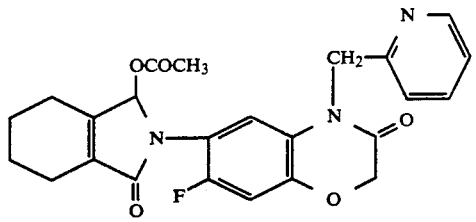

The product (1 g) obtained in Example 2 was dissolved in chloroform (20 ml). To this solution were added trimethylamine (0.5 g) and then acetic acid anhydride (0.5 g) at a temperature of 10° to 20° C. The reaction mixture was stirred at room temperature for 30 minutes, admixed with a 2% aqueous solution of hydrochloric acid (10 ml). The organic layer was separated, washed with water, dried over anhydrous sodium sulfate. After the solvent had been distilled off, the aimed product i.e. 6-(3-acetoxy-4,5,6,7-tetrahydroisoindolin-1-on-2-yl)-7-fluoro-4 (pyridin-2-ylmethyl)-2H-1,4-benzoxazin-3(4H)-one (1 g) was obtained. $n_D^{20} = 1.5725$

EXAMPLE 4

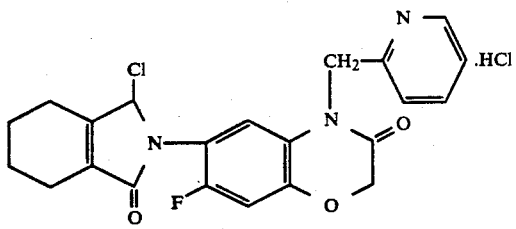

The compound (4.1 g) obtained in Example 2 was dissolved in chloroform (40 ml). To this solution was added thionyl chloride (1.4 g) at a temperature of 10° to 20° C. The reaction mixture was stirred at room temperature for 30 minutes, and then further stirred at a temperature of 30° to 40° C. for 2 hours. Thereafter, the reaction mixture was cooled to a temperature of 10° to 15° C. to form a crystalline product, which was then collected by filtration, washed in chloroform (10 ml) and dried, so that the aimed product i.e. 6-(3-chloro-4,5,6,7-tetrahydroisoindolin-1-on-2-yl)-7-fluoro-4-(pyridin-2-ylmethyl)-2H-1,4-benzoxazin-3(4H)-one hydrochloride (4.1 g) was obtained.

The compound obtained in Example 4 is highly reactive, so that it is possible to react the compound with various nucleophilic agents in the presence of a base such as triethylamine.

For instance, a reaction of the compound of Example 4 with ethanol results in the formation of 6-(3-ethoxy-4,5,6,7-tetrahydroisoindolin-1-on-2-yl)-7-fluoro-4-(pyridin-2-ylmethyl)-2H-1,4-benzoxazin-3(4H)-one. When the compound of Example 4 is reacted with ethanethiol, then 6-(3-ethylthio-4,5,6,7-tetrahydroisoindolin-1-on-2-yl)-7-fluoro-4-(pyridin-2-ylmethyl)-2H-1,4-benzoxazin-3(4H)-one will be formed. When the compound of Example 4 is reacted with dimethylamine, then 6-(3-N,N-dimethylamino-4,5,6,7-tetrahydroisoindolin-1-on-2-yl)-7-fluoro-4-(pyridin-2-ylmethyl)-2H-1,4-benzoxazin-3(4H)-one will be formed. When the compound of Example 4 is reacted with anhydrous potassium fluoride in dimethylsulfoxide, then a halogen exchange reaction will occur, so that 6-(3-fluoro-4,5,6,7-tetrahydroisoindolin-1-on-2-yl)-7-fluoro-4-(pyridin-2-ylmethyl)-2H-1,4-benzoxazin-3(4H)-one may be obtained.

EXAMPLE 5

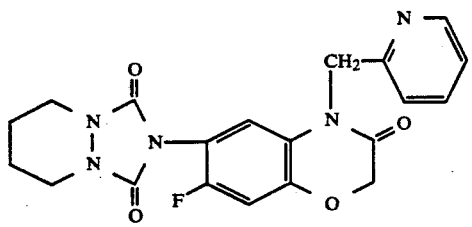

7-fluoro-6-isocyanato-4-(pyridin-2-ylmethyl)-2H-1,4-benzoxazin-3-(4H)-one hydrochloride (2 g) was suspended in tetrahydrofuran (50 ml). To this suspension was added triethylamine (0.61 g) and 1-ethoxycarbonylhexahydropyridazine (1.2 g) successively. The reaction mixture was stirred at a temperature of 10° to 20° C., and filtered to remove the triethylamine hydrochloride. The filtrate was concentrated, so that a viscous liquid (2.3 g) was obtained. This product was analyzed by means of NMR and IR-spectroscopy. It was a urea compound of the formula:

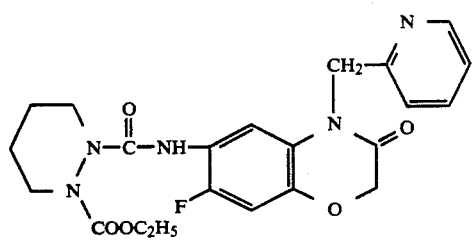

The urea compound (2.2 g) was mixed with ethanol (10 ml) which contained a catalytic amount of sodium ethoxide. This mixture was heated under reflux for 3 hours, and cooled to a temperature of 0° to 10° C. to form a crystalline product, which was collected by filtration, washed with a small amount of ethanol, and dried. The aimed product i.e. 7-fluoro-4-(pyridin-2-ylmethyl)-6-(1,2-tetramethylene-urazol-4-yl)-2H-1,4-benzoxazin-3(4H)-one (1.53 g) was obtained. m.p. 200°–201° C.

EXAMPLE 6

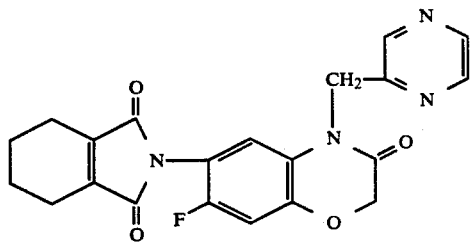

A mixture of 2-methylpyrazine (5.64 g), α,α'-azobis-(isobutyronitrile) (0.05 g), N-chloro-succinimide (2.7 g) and carbon tetrachloride (100 ml) was heated under reflux and under the radiation of light from an electric incandescent lamp (100 V; 300 W) for 4 hours according to a known method described in J. Org. Chem., vol. 38, p. 2049. The reaction mixture was cooled to a temperature of 10° of 20° C., and filtered. The filtrate was concentrated to obtain a mixture (4.4 g) of 2-(chloromethyl)pyrazine and 2-methylpyrazine. The molar ratio of the former compound to the latter was determined by H-NMR-analysts. The molar ratio in question was 1:2. The mixture was admixed with 7-fluoro-6-(4,5,6,7-tetrahydro-2H-isoindole-1,3-dion-2-yl)-2H-1,4-benzoxazin-3(4H)-one (3.9 g) (which was prepared according to a method disclosed in EP-OS No. 170,191), potassium carbonate (2 g) and acetonitrile (100 ml), and heated under reflux for 4 hours. The mixture was allowed to cool, and then distilled under a reduced pressure to remove the substances having lower boiling points from the mixture.

The resulting residue was mixed with toluene (150 ml), then admixed with water (100 ml) and stirred. After that, the organic layer was separated, washed with a 5% aqueous potassium hydroxide solution and then with water, and dried over anhydrous sodium sulfate. The solvent was distilled off under a reduced pressure. The residue thus obtained was recrystallized from ethanol, so that the aimed compound i.e. 7-fluoro-4-(pyrazin-2-ylmethyl)-6-(4,5,6,7-tetrahydro-2H-isoindole-1,3-dion- 2-yl)-2H-1,4-benzoxazin-3(4H)-one (1.72 g) was obtained. m.p. 191°-194° C.

EXAMPLE 7

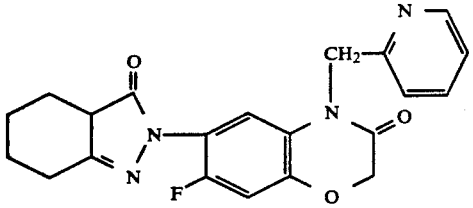

A mixture of 7-fluoro-6-hydrazino-4-(pyridin-2-ylmethyl)-2H-1,4-benzoxazin-3-3(4H)-one (1.49 g), 2-ethoxycarbonyl-cyclohexanone (0.9 g) and ethanol (20 ml) was admixed with a catalytic amount of sodium ethoxide, and heated under reflux for 5 hours. The reaction mixture was distilled to remove the ethanol therefrom, admixed with toluene (30 ml), heated under reflux for 10 minutes, cooled to a temperature of 0° to 10° C., and filtered. The solid portion thus obtained was washed with n-hexane, and dried, so that the aimed compound, i.e. 7-fluoro-6-(3,3a,,4,5,6,7-hexahydro-2H-indazole-3-on-2-yl)-4-(pyridin-2-ylmethyl)-2H-1,4-benzoxazin-3(4H)-one (1.24 g) was obtained. m.p. 216°-219° C.

EXAMPLE 8

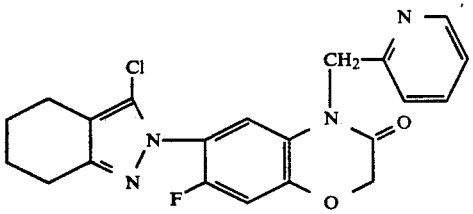

A mixture of 7-fluoro-6-(3,3a,4,5,6,7-hexahydro-2H-indazol-3-on-2-yl)-4-(pyridin-2-yl-methyl)-2H-1,4-benzoxazin-3(4H)-one (1.24 g), phosgene (0.62 g) and toluene (20 ml) was added with one drop of N,N-dimethylformamide. The reaction mixture was heated under reflux for 5 hours, cooled to a lower temperature, distilled under a reduced pressure to remove the solvent therefrom. The resultant residue was mixed with ethyl acetate (100 ml) and with a saturated aqueous sodium bicarbonate solution (20 ml). The liquid mixture thus obtained was stirred, and the organic layer was separated, dried over anhydrous sodium sulfate, and distilled to remove the ethyl acetate. The resulting residue was worked up by means of a silica gel column chromatography (eluant: toluene/tetrahydrofuran=4/1), so that the aimed compound i.e. 7-fluoro-6-(3-chloro-4,5,6,7-tetrahydro-2H-indazol-2-yl)-4-(pyridin-2-ylmethyl)-2H-1,4-benzoxazin-3(4H)-one (0.8 g) was obtained. m.p. 198°-201° C.

EXAMPLE 9

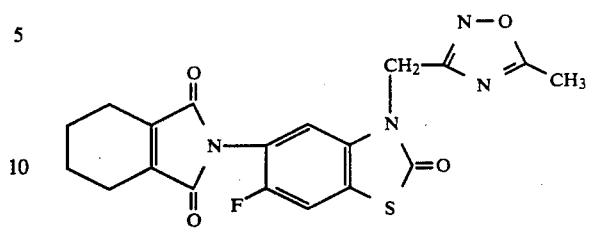

A mixture of 5-amino-6-fluoro-3-(5-methyl-1,2,4-oxadiazol-3-ylmethyl)-2(3H)-benzothiazolone (2.8 g) and acetic acid (20 ml) was admixed with 3,4,5,6-tetrahydrophthalic anhydride (1.6 g), stirred at a temperature of 20° to 30° C. for 30 minutes, and then heated under refluxing for 2 hours. The reaction mixture was distilled under a reduced pressure to remove the acetic acid therefrom, and the residue was worked up by chromatography, wherein a silica gel column was used together with an eluant comprising a tetrahydrofuran/toluene mixture (a 1:3 mixture), so that the aimed compound, i.e. 6-fluoro-3-(5-methyl-1,2,4-oxadiazol-3-ylmethyl)-5-(4,5,6,7-tetrahydro-2H-isoindole-1,3-dion-2-yl)-2(3H)-benzothiazolone (2.9 g) was obtained. m.p. 198°-199° C.

EXAMPLE 10

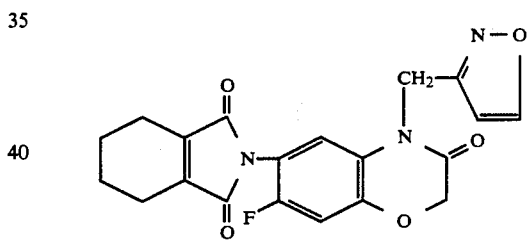

A compound of 3-(chloromethyl)-isoxazole (1.2 g) was added dropwise at a temperature of 20° to 30° C. under stirring to a mixture of 7-fluoro-6-(4,5,6,7-tetrahydro-2H-isoindole-1,3-dion-2-yl)-2H-1,4-benzoxazin-3(4H)-one (3.16 g), acetonitrile (50 ml) and potassium carbonate (1.5 g). The reaction mixture was heated under refluxing for 3 hours, cooled to room temperature, and filtered. The filtrate was concentrated under a reduced pressure to dryness. The resultant residue was mixed with toluene (150 ml) to form a suspension, which was then filtered to remove the undissolved materials therefrom. The filtrate was concentrated under a reduced pressure so as to obtain a viscous material, which was thereafter dissolved in a minimum amount of ethanol. The ethanol solution was cooled to precipitate a crystalline product. This product was separated by filtration and dried, so that the aimed compound, i.e. 7-fluoro-4-(isoxazol-3-ylmethyl)-6-(4,5,6,7-tetrahydro-2H-isoindole-1,3-dion-2-yl)-2H-1,4-benzoxazin-3(4H)-one (3.3 g) was obtained. m.p. 206°-210° C.

EXAMPLE 11

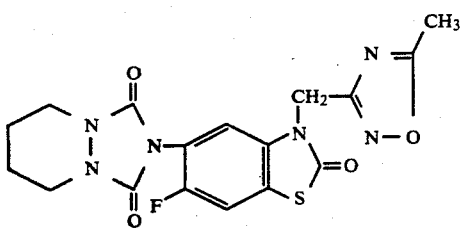

A compound of 5-isocyanato-6-fluoro-3-(5-methyl-1,2,4-oxadiazol-3-ylmethyl)-2(3H)-benzothiazolone (0.73 g) was dissolved in tetrahydrofuran (15 ml). To the resulting solution was dropwise added 1-ethoxycarbonyl-hexahydropyridazine (0.4 g) at room temprature. The reaction mixture was allowed to stand over night, and then distilled to remove the solvent therefrom, so that a porous material (1.08 g) was obtained. This material (1 g) was dissolved in ethanol (30 ml), and the resultant solution was admixed with a catalytic amount of sodium ethoxide, heated under reflux for 1.5 hours, and then cooled to a temperature of 0° to 10° C. The crystalline product thus formed was separated by means of filtration, washed with a small amount of cold ethanol, and dried, so that the aimed compound, i.e. 6-fluoro-3-(5-methyl-1,2,4-oxadiazol-3-ylmethyl)-5-(1,2-tetramethylene-1,2,4-triazolidine-3,5-dion-4yl)-2(3H)-benzothiazolone (0.75 g) was obtained. m.p. 251°–255° C.

In the process of Example 3, the above-mentioned isocyanate derivative may be replaced by 5-isothiocyanato-6-fluoro-3-(5-methyl-1,2,4-oxadiazol-3-ylmethyl)-2(3H)-benzothiazolone, so that the aimed compound, i.e. 6-fluoro-5-(1,2-tetramethylene-1,2,4-triazolidin-3-one-5-thion-4-yl)-3-(5-methyl-1,2,4-oxadiazol-3-yl-methyl)-2(3H)-benzothiazolone can be obtained in a high yield.

EXAMPLE 12

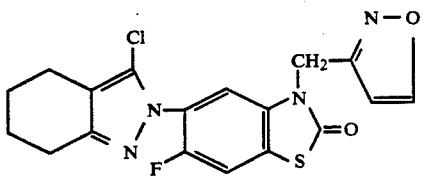

A mixture of 6-fluoro-5-hydrazino-3-(isoxazol-3-ylmethyl)-2(3H)-benzothiazolone (2.8 g), 2-ethoxycarbonyl-cyclohexanone (1.8 g), sodium ethoxide (0.03 g) and ethanol (40 ml) was heated under reflux for 5 hours. The ethanol was distilled off, and the residue was admixed with toluene (50 ml). The solution thus formed was heated under refluxing for 10 minutes, cooled to a temperature of 0° to 10° C. to precipitate a solid product, which was collected by filtration and washed with n-hexane. The aimed intermediate compound, i.e. 6-fluoro-5-(3,3a,4,5,6,7-hexahydro-2H-indol-3-one-2-yl)-3-(isoxazol-3-ylmethyl)-2(3H)-benzothiazolone (3.1 g) was obtained.

The whole amount of the intermediate compound was admixed with toluene (100 ml), trichloromethyl chloroformate (1.5 g) and N,N-dimethylformamide (0.05 g), and the resulting mixture was heated under refluxing for 5 hours. The components, having lower boiling points, were distilled off, and the residue was admixed with ethyl acetate (150 ml). The resulting solution was washed with an aqueous solution of sodium bicarbonate, dried over anhydrous sodium sulfate, and distilled to remove the solvent therefrom.

The residue was worked up by a silica gel column chromatography (eluant: tetrahydrofuran/toluene=¼), so that the aimed compound, i.e. 6-fluoro-5-(3-chloro-4,5,6,7-tetrahydro-2H-indol-2-yl)-3-(isoxazol-3-ylmethyl)-2(3H)-benzothiazolone (1.8 g) was obtained as a porous material.

According to the same methods as in the above examples, the compounds of the formula (I) can be obtained as shown in the following Tables 1 to 14, together with the compounds obtained in Examples 1 to 12.

TABLE 1

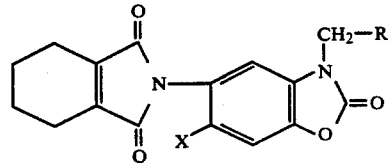

| Compound No. | X | R | |
|---|---|---|---|
| 1 | F | 5-methoxy-1,2,4-thiadizol-3-yl | |
| 2 | F | 5-ethoxy-1,2,4-thiadiazol-3-yl | |
| 3 | F | 5-propoxy-1,2,4-thiadiazol-3-yl | |
| 4 | F | 5-isopropoxyy-1,2,4-thiadiazol-3-yl | |
| 5 | F | 5-butoxy-1,2,4-thiadiazol-3-yl | |
| 6 | F | 5-dimethylamino-1,2,4-thiadiazol-3-yl | |
| 7 | F | 1,2,5-thiadiazol-3-yl | |
| 8 | F | 3-chloro-1,2,5-thiadiazol-4-yl | |
| 9 | F | 3-methyl-1,2,5-thiadiazol-4-yl | |
| 10 | F | 2-amino-1,3,4-thiadiazol-5-yl | |
| 11 | F | 2-chloro-1,3,4-thiadiazol-5-yl | |
| 12 | F | 2-methoxy-1,3,4-thiadiazol-5-yl | |
| 13 | F | 2-methylthio-1,3,4-thiadiazol-5-yl | |
| 14 | F | 2-methyl-1,3,4-thiadiazol-5-yl | |
| 15 | F | 1,3-thiazol-2-yl | |
| 16 | F | 5-chloro-1,3-thiadiazol-2-yl | |
| 17 | F | 4,5-dichloro-1,3-thiadiazol-2-yl | |
| 18 | F | 3-methyl-1,3-thiazol-2-yl | |
| 19 | F | 5-chloro-4-methyl-1,3-thiazol-2-yl | |
| 20 | F | 4,5-dimethyl-1,3-thiazol-2-yl | |
| 21 | F | 1,3-thiazol-4-yl | |
| 22 | F | 2-amino-1,3-thiazol-4-yl | |
| 23 | F | 2-acetamido-1,3-thiazol-4-yl | |
| 24 | F | 2-chloro-1,3-thiazol-4-yl | |
| 25 | F | 2-methyl-1,3-thiazol-4-yl | |
| 26 | F | 2-trifluoromethyl-1,3-thiazol-4-yl | |
| 27 | F | 2-ethyl-1,3-thiazol-4-yl | |
| 28 | F | 1,2,3-thiadiazol-4-yl | |
| 29 | F | 5-chloro-1,2,3-thiadiazol-4-yl | |
| 30 | F | 5-methyl-1,2,3-thiadiazol-4-yl | |
| 31 | F | 5-methyl-1,2,4-oxadiazol-3-yl | m.p. 188–193° C. |
| 32 | F | 5-methoxymethyl-1,2,4-oxadiazol-3-yl | |
| 33 | F | 5-ethyl-1,2,4-oxadiazol-3-yl | |
| 34 | F | 3-methyl-1,2,4-oxadiazol-5-yl | |
| 35 | F | 3-trifluoromethyl-1,2,4-oxadiazol-5-yl | |
| 36 | F | 3-ethyl-1,2,4-oxadiazol-5-yl | |
| 37 | F | 3-isopropyl-1,2,4-oxadiazol-5-yl | |
| 38 | F | 3-methyl-1,2,5-oxadiazol-4-yl | |
| 39 | F | 1,3,4-oxadiazol-2-yl | |
| 40 | F | 2-methyl-1,3,4-oxadiazol-5-yl | |
| 41 | F | 2-ethyl-1,3,4-oxadiazol-5-yl | |
| 42 | F | 1,2-thiazol-3-yl | |
| 43 | F | 4-chloro-1,2-thiazol-3-yl | |
| 44 | F | 4-bromo-1,2-thiazol-3-yl | |
| 45 | F | 2-furyl | |
| 46 | F | 3-furyl | |
| 47 | F | 2-thienyl | |
| 48 | F | 3-thienyl | |
| 49 | F | 1-methylpyrazol-3-yl | |
| 50 | F | 4,5-dichloro-1-methylpyrazol-3-yl | |

TABLE 1-continued

| Compound No. | X | R | |
|---|---|---|---|
| 51 | F | 1-methylimidazol-2-yl | |
| 52 | F | 1-methylimidazol-4-yl | |
| 53 | F | 1-methylimidazol-5-yl | |
| 54 | F | 1-methyl-1,2,4-triazol-3-yl | |
| 55 | F | 1-methyl-1,3,4-triazol-2-yl | |
| 56 | F | 1-methyl-1,2,3,4-tetrazol-5-yl | |
| 57 | F | 1,2-oxazol-3-yl | m.p. 189–191.5° C. |
| 58 | F | 5-methyl-1,2-oxazol-3-yl | |
| 59 | F | 3-methyl-1,2-oxazol-5-yl | |
| 60 | H | 1-methyl-1,2,4-triazol-3-yl | m.p. 134–139° C. |
| 61 | H | 1,2-oxazol-3-yl | |
| 62 | H | 5-methyl-1,2-oxazol-3-yl | |
| 63 | H | 5-methyl-1,2,4-oxadiazol-3-yl | |
| 64 | H | 3-methyl-1,2,4-oxadiazol-5-yl | |
| 65 | H | 3-methyl-1,2,5-oxadiazol-4-yl | |
| 66 | H | 1,3,4-oxadiazol-2-yl | |
| 67 | H | 2-methyl-1,3,4-oxadiazol-5-yl | |
| 68 | H | 1,3-thiazol-4-yl | |
| 69 | H | 2-methyl-1,3-thiazol-4-yl | |
| 70 | H | 5-methoxy-1,2,4-thiadiazol-3-yl | |
| 71 | H | 1,2,5-thiadiazol-3-yl | |
| 72 | H | 3-methyl-1,2,5-thiadiazol-4-yl | |
| 73 | H | 2-methyl-1,3,4-thiadiazol-5-yl | |

TABLE 2

| Compound No. | X | R | |
|---|---|---|---|
| 74 | F | 1-methyl-1,2,4-triazol-3-yl | |
| 75 | F | 1,2-oxazol-3-yl | m.p. 154–155° C. |
| 76 | F | 5-methyl-1,2-oxazol-3-yl | |
| 77 | F | 5-methyl-1,2,4-oxazol-3-yl | m.p. 180–182° C. |
| 78 | F | 3-methyl-1,2,4-oxazol-5-yl | |
| 79 | F | 1,3-thiazol-4-yl | |
| 80 | F | 2-methyl-1,3-thiazol-4-yl | |
| 81 | F | 2-methyl-1,3,4-thiadiazol-5-yl | |
| 82 | H | 1-methyl-1,2,4-triazol-3-yl | |
| 83 | H | 1,2-oxazol-3-yl | m.p. 190–191° C. |
| 84 | H | 5-methyl-1,2-oxazol-3-yl | |
| 85 | H | 5-methyl-1,2,4-oxazol-3-yl | |
| 86 | H | 3-methyl-1,2,4-oxazol-5-yl | |
| 87 | H | 1,3-thiazol-4-yl | |
| 88 | H | 2-methyl-1,3-thiazol-4-yl | |
| 89 | H | 2-methyl-1,3,4-thiadiazol-5-yl | |

TABLE 3

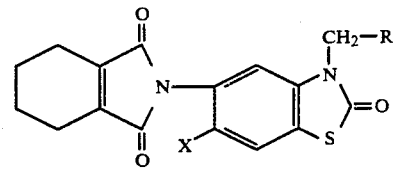

| Compound No. | X | R | |
|---|---|---|---|
| 90 | F | 5-methoxy-1,2,4-thiadiazol-3-yl | amorphous |
| 91 | F | 5-ethoxy-1,2,4-thiadiazol-3-yl | m.p. 83–89° C. |
| 92 | F | 5-propoxy-1,2,4-thiadiazol-3-yl | |
| 93 | F | 5-isopropoxy-1,2,4-thiadiazol-3-yl | |
| 94 | F | 5-butoxy-1,2,4-thiadiazol-3-yl | |
| 95 | F | 5-dimethylamino-1,2,4-thiadiazol-3-yl | |
| 96 | F | 1,2,5-thiadiazol-3-yl | |
| 97 | F | 3-chloro-1,2,5-thiadiazol-4-yl | |
| 98 | F | 3-methyl-1,2,5-thiadiazol-4-yl | |
| 99 | F | 2-amino-1,3,4-thiadiazol-5-yl | |
| 100 | F | 2-chloro-1,3,4-thiadiazol-5-yl | |
| 101 | F | 2-methoxy-1,3,4-thiadiazol-5-yl | |
| 102 | F | 2-methylthio-1,3,4-thiadiazol-5-yl | |
| 103 | F | 2-methyl-1,3,4-thiadiazol-5-yl | |
| 104 | F | 1,3-thiazol-2-yl | |
| 105 | F | 5-chloro-1,3-thiadiazol-2-yl | |
| 106 | F | 4,5-dichloro-1,3-thiadiazol-2-yl | |
| 107 | F | 3-methyl-1,3-thiazol-2-yl | |
| 108 | F | 5-chloro-4-methyl-1,3-thiazol-2-yl | |
| 109 | F | 4,5-dimethyl-1,3-thiazol-2-yl | |
| 110 | F | 1,3-thiazol-4-yl | m.p. 168–170° C. |
| 111 | F | 2-amino-1,3-thiazol-4-yl | |
| 112 | F | 2-acetamido-1,3-thiazol-4-yl | |
| 113 | F | 2-chloro-1,3-thiazol-4-yl | |
| 114 | F | 2-methyl-1,3-thiazol-4-yl | |
| 115 | F | 2-trifluoromethyl-1,3-thiazol-4-yl | |
| 116 | F | 2-ethyl-1,3-thiazol-4-yl | |
| 117 | F | 1,2,3-thiadiazol-4-yl | |
| 118 | F | 5-chloro-1,2,3-thiadiazol-4-yl | |
| 119 | F | 5-methyl-1,2,3-thiadiazol-4-yl | |
| 120 | F | 5-methyl-1,2,4-oxadiazol-3-yl | m.p. 198–199° C. |
| 121 | F | 5-methoxymethyl-1,2,4-oxadiazol-3-yl | |
| 122 | F | 5-ethyl-1,2,4-oxadiazol-3-yl | m.p. 83–89° C. |
| 123 | F | 3-methyl-1,2,4-oxadiazol-5-yl | m.p. 191–193° C. |
| 124 | F | 3-ethyl-1,2,4-oxadiazol-5-yl | |
| 125 | F | 3-trifluoromethyl-1,2,4-oxadiazol-5-yl | |
| 126 | F | 3-methoxymethyl-1,2,4-oxadiazol-5-yl | |
| 127 | F | 3-methyl-1,2,5-oxadiazol-4-yl | m.p. 166–170° C. |
| 128 | F | 1,3,4-oxadiazol-2-yl | |
| 129 | F | 2-methyl-1,3,4-oxadiazol-5-yl | |
| 130 | F | 2-ethyl-1,3,4-oxadiazol-5-yl | |
| 131 | F | 1,2-thiadiazol-3-yl | |
| 132 | F | 4-chloro-1,2-thiazol-3-yl | |
| 133 | F | 4-bromo-1,2-thiazol-3-yl | |
| 134 | F | 2-furyl | |
| 135 | F | 3-furyl | |
| 136 | F | 2-thienyl | |
| 137 | F | 3-thienyl | |
| 138 | F | 1-methylpyrazol-3-yl | |
| 139 | F | 4,5-dichloro-1-methylpyrazol-3-yl | |
| 140 | F | 1-methyl-imidazol-2-yl | |
| 141 | F | 1-methyl-imidazol-4-yl | |
| 142 | F | 1-methyl-imidazol-5-yl | |
| 143 | F | 1-methyl-1,2,4-triazol-3-yl | |
| 144 | F | 1-methyl-1,3,4-triazol-2-yl | |
| 145 | F | 1-methyl-1,2,3,4-tetrazol-5-yl | |
| 146 | F | 1,2-oxazol-3-yl | m.p. 196–200° C. |
| 147 | F | 5-methyl-1,2-oxazol-3-yl | |
| 148 | F | 3-methyl-1,2-oxazol-5-yl | amorphous |
| 149 | H | 1-methyl-1,2,4-triazol-3-yl | |
| 150 | H | 1,2-oxazol-3-yl | |
| 151 | H | 5-methyl-1,2-oxazol-3-yl | |
| 152 | H | 5-methyl-1,2,4-oxadiazol-3-yl | |

TABLE 3-continued

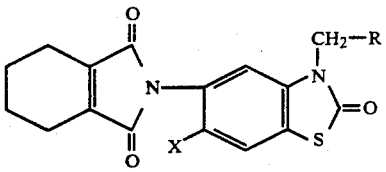

| Compound No. | X | R | |
|---|---|---|---|
| 153 | H | 3-methyl-1,2,4-oxadiazol-5-yl | |
| 154 | H | 1,3-thiazol-4-yl | |
| 155 | H | 2-methyl-1,3-thiazol-4-yl | |
| 156 | H | 2-methyl-1,3,4-thiadiazol-5-yl | |
| 157 | F | 3-isopropyl-1,2,4-oxadiazol-5-yl | |
| 158 | F | 2-tetrahydrofuryl | $n_D^{20}$ 1.5675 |
| 159 | F | pyridin-2-yl | m.p. 176–180° C. |
| 160 | F | pyridazin-3-yl | |
| 161 | F | pyrimidin-4-yl | |
| 162 | F | pyrazin-2-yl | m.p. 100–102° C. |
| 163 | F | pyrimidin-2-yl | |
| 164 | F | 1,3,5-triazin-2-yl | |
| 165 | F | cyclopropyl | m.p. 110–115° C. |
| 166 | F | 1,2,4-triazol-1-yl | m.p. 188–192° C. |
| 166a | F | 1,2,5-thiadiazol-3-yl | m.p. 100–105° C. |

TABLE 4

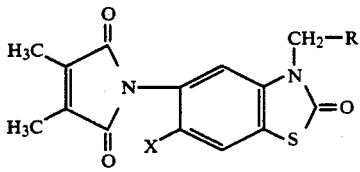

| Compound No. | X | R | |
|---|---|---|---|
| 167 | F | 1-methyl-1,2,4-triazol-3-yl | |
| 168 | F | 1,2-oxazol-3-yl | |
| 169 | F | 1,2-oxazol-5-yl | m.p. 219–220° C. |
| 170 | F | 5-methyl-1,2,4-oxazol-3-yl | |
| 171 | F | 3-methyl-1,2,4-oxazol-5-yl | |
| 172 | F | 1,3-thiazol-4-yl | |
| 173 | F | 2-methyl-1,3-thiazol-4-yl | |
| 174 | F | 2-methyl-1,3,4-thiadiazol-5-yl | |
| 175 | F | cyclopropyl | m.p. 171–173° C. |
| 176 | F | pyridin-2-yl | m.p. 180–188° C. |

TABLE 5

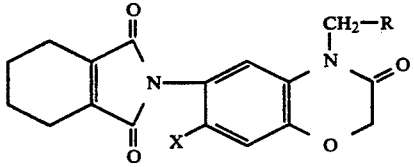

| Compound No. | X | R | |
|---|---|---|---|
| 177 | F | 2-tetrahydrofuryl | |
| 178 | F | 5-methoxy-1,2,4-thiadiazol-3-yl | amorphous |
| 179 | F | 5-ethoxy-1,2,4-thiadiazol-3-yl | m.p. 121–124° C. |
| 180 | F | 5-propoxy-1,2,4-thiadiazol-3-yl | |
| 181 | F | 5-isopropoxy-1,2,4-thiadiazol-3-yl | |
| 182 | F | 5-dimethylamino-1,2,4-thiadiazol-3-yl | |
| 183 | F | 1,2,5-thiadiazol-3-yl | m.p. 215–220° C. |

TABLE 5-continued

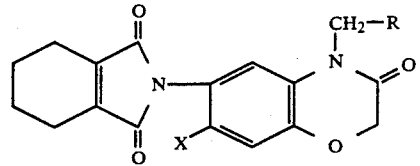

| Compound No. | X | R | |
|---|---|---|---|
| 184 | F | 3-chloro-1,2,5-thiadiazol-4-yl | |
| 185 | F | 3-methyl-1,2,5-thiadiazol-4-yl | |
| 186 | F | 2-amino-1,3,4-thiadiazol-5-yl | |
| 187 | F | 2-chloro-1,3,4-thiadiazol-5-yl | |
| 188 | F | 2-methoxy-1,3,4-thiadiazol-5-yl | |
| 189 | F | 2-methylthio-1,3,4-thiadiazol-5-yl | |
| 190 | F | 2-methyl-1,3,4-thiadiazol-5-yl | |
| 191 | F | 1,3-thiazol-2-yl | |
| 192 | F | 5-chloro-1,3-thiadiazol-2-yl | |
| 193 | F | 4,5-dichloro-1,3-thiadiazol-2-yl | |
| 194 | F | 3-methyl-1,3-thiazol-2-yl | |
| 195 | F | 5-chloro-4-methyl-1,3-thiazol-2-yl | |
| 196 | F | 4,5-dimethyl-1,3-thiazol-2-yl | |
| 197 | F | 1,3-thiazol-4-yl | m.p. 200–202° C. |
| 198 | F | 2-amino-1,3-thiazol-4-yl | |
| 199 | F | 2-acetamido-1,3-thiazol-4-yl | |
| 200 | F | 2-chloro-1,3-thiazol-4-yl | |
| 201 | F | 2-methyl-1,3-thiazol-4-yl | |
| 202 | F | 2-trifluoromethyl-1,3-thiazol-4-yl | |
| 203 | F | 2-ethyl-1,3-thiazol-4-yl | |
| 204 | F | 1,2,3-thiadiazol-4-yl | |
| 205 | F | 5-chloro-1,2,3-thiadiazol-4-yl | |
| 206 | F | 5-methyl-1,2,3-thiadiazol-4-yl | |
| 207 | F | 5-methyl-1,2,4-oxadiazol-3-yl | m.p. 200–205° C. |
| 208 | F | 5-methoxymethyl-1,2,4-oxadiazol-3-yl | |
| 209 | F | 5-ethyl-1,2,4-oxadiazol-3-yl | m.p. 74–79° C. |
| 210 | F | 3-propyl-1,2,4-oxadiazol-5-yl | |
| 211 | F | 3-methyl-1,2,4-oxadiazol-5-yl | m.p. 196–201° C. |
| 212 | F | 3-trifluoromethyl-1,2,4-oxadiazol-5-yl | |
| 213 | F | 3-ethyl-1,2,4-oxadiazol-5-yl | m.p. 74–79° C. |
| 214 | F | 3-methyl-1,2,5-oxadiazol-4-yl | m.p. 190–194° C. |
| 215 | F | 1,3,4-oxadiazol-2-yl | |
| 216 | F | 2-methyl-1,3,4-oxadiazol-5-yl | |
| 217 | F | 2-ethyl-1,3,4-oxadiazol-5-yl | |
| 218 | F | 1,2-thiazol-3-yl | |
| 219 | F | 4-chloro-1,2-thiazol-3-yl | |
| 220 | F | 4-bromo-1,2-thiazol-3-yl | |
| 221 | F | 2-furyl | |
| 222 | F | 3-furyl | |
| 223 | F | 2-thienyl | m.p. 160–162° C. |
| 224 | F | 3-thienyl | m.p. 167–171° C. |
| 225 | F | 1-methylpyrazol-3-yl | |
| 226 | F | 4,5-dichloro-1-methylpyrazol-3-yl | |
| 227 | F | 1-methyl-imidazol-2-yl | |
| 228 | F | 1-methyl-imidazol-4-yl | |
| 229 | F | 1-methyl-imidazol-5-yl | |
| 230 | F | 1-methyl-1,2,4-triazol-3-yl | |
| 231 | F | 1-methyl-1,3,4-triazol-2-yl | |
| 232 | F | 1-methyl-1,2,3,4-tetrazol-5-yl | m.p. 206–210° C. |
| 233 | F | 1,2-oxazol-3-yl | |
| 234 | F | 5-methyl-1,2-oxazol-3-yl | |
| 235 | F | 3-methyl-1,2-oxazol-5-yl | m.p. 194–195° C. |
| 236 | H | 1-methyl-1,2,4-triazol-3-yl | m.p. 219–225° C. |
| 237 | H | 1,2-oxazol-3-yl | m.p. 208–212° C. |
| 238 | H | 5-methyl-1,2-oxazol-3-yl | m.p. 189–195° C. |
| 239 | H | 5-methyl-1,2,4-oxadiazol-3-yl | m.p. 160–167° C. |
| 240 | H | 3-methyl-1,2,4-oxadiazol-5-yl | m.p. 195–199° C. |
| 241 | H | 1,3-thiazol-4-yl | m.p. 140–143° C. |
| 242 | H | 2-methyl-1,3-thiazol-4-yl | |
| 243 | H | 2-methyl-1,3,4-thiadiazol-5-yl | |
| 244 | F | 3-isopropyl-1,2,4-oxadiazol-5-yl | amorphous |
| 245 | H | 5-ethoxy-1,2,4-thiadiazol-3-yl | m.p. 112–125° C. |
| 246 | H | 4-methyl-1,2,5-oxadiazol-3-yl | m.p. 194–197° C. |
| 247 | H | pyridin-2-yl | m.p. 185–188° C. |
| 248 | F | pyridin-2-yl | m.p. 188–190° C. |
| 249 | F | 6-chloropyridin-2-yl | m.p. 97–100° C. |
| 250 | F | 4-chloropyridin-2-yl | |
| 251 | F | 4-fluoropyridin-2-yl | |

TABLE 5-continued

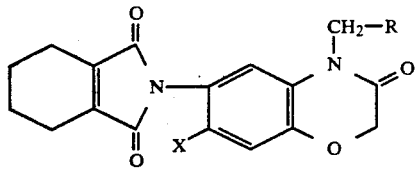

| Compound No. | X | R | |
|---|---|---|---|
| 252 | F | 5-chloropyridin-2-yl | |
| 253 | F | 4-methylpyridin-2-yl | |
| 254 | F | 5-methylpyridin-2-yl | |
| 255 | F | pyridazin-3-yl | |
| 256 | F | pyrimidin-4-yl | |
| 257 | F | pyrazin-2-yl | m.p. 191–194° C. |
| 258 | F | pyrimidin-2-yl | |
| 259 | F | 4-chloro-6-methylpyrimidin-2-yl | |
| 260 | F | 4,6-dimethylpyrimidin-2-yl | |
| 261 | F | 1,3,5-triazin-2-yl | |

TABLE 6

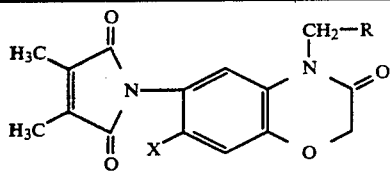

| Compound No. | X | R | |
|---|---|---|---|
| 262 | F | 1-methyl-1,2,4-triazol-3-yl | |
| 263 | F | 1,2-oxazol-3-yl | m.p. 256–258° C. |
| 264 | F | 5-methyl-1,2-oxazol-3-yl | |
| 265 | F | 5-methyl-1,2,4-oxadiazol-3-yl | m.p. 184–190° C. |
| 266 | F | 5-ethyl-1,2,4-oxadiazol-3-yl | m.p. 105–115° C. |
| 267 | F | 3-methyl-1,2,5-oxadiazol-4-yl | |
| 268 | F | 1,3,4-oxadiazol-2-yl | |
| 269 | F | 2-methyl-1,3,4-oxadiazol-5-yl | |
| 270 | F | 1,3-thiazol-4-yl | m.p. 172–174° C. |
| 271 | F | 2-methyl-1,3-thiazol-4-yl | m.p. 137–141° C. |
| 272 | F | 5-methoxy-1,2,4-thiadiazol-3-yl | m.p. 145–150° C. |
| 273 | F | 1,2,5-thiadiazol-3-yl | |
| 274 | F | 3-methyl-1,2,5-thiadiazol-4-yl | |
| 275 | F | 2-methyl-1,3,4-thiadiazol-5-yl | |
| 276 | H | 1-methyl-1,2,4-triazol-3-yl | |
| 277 | H | 1,2-oxazol-3-yl | |
| 278 | H | 5-methyl-1,2-oxazol-3-yl | |
| 279 | H | 5-methyl-1,2,4-oxazol-3-yl | |
| 280 | H | 3-methyl-1,2,4-oxazol-5-yl | m.p. 209–215° C. |
| 281 | H | 1,3-thiazol-4-yl | |
| 282 | H | 2-methyl-1,3-thiazol-4-yl | |
| 283 | H | 2-methyl-1,3,4-thiadiazol-5-yl | |
| 284 | F | pyridin-2-yl | m.p. 140–141° C. |
| 284a | H | cyclopropyl | amorphous |
| 284b | F | cyclopropyl | m.p. 105–107° C. |

TABLE 7

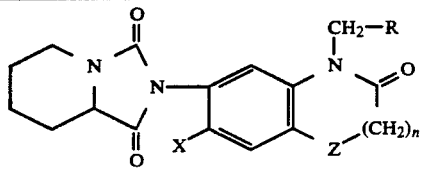

| Compound No. | X | Z | n | R | |
|---|---|---|---|---|---|
| 285 | H | O | 0 | 1,2-oxazol-5-yl | |
| 286 | F | O | 0 | 1,2-oxazol-5-yl | |

TABLE 7-continued

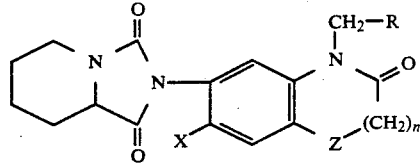

| Compound No. | X | Z | n | R | |
|---|---|---|---|---|---|
| 287 | H | O | 1 | 1,2-oxazol-5-yl | |
| 288 | H | O | 1 | 5-methyl-1,2,4-oxadiazol-3-yl | |
| 289 | F | O | 1 | 1,2-oxazol-3-yl | m.p. 155–162° C. |
| 290 | F | O | 1 | 5-methyl-1,2,4-oxadiazol-3-yl | amorphous |
| 291 | F | S | 0 | 1,2-oxazol-3-yl | m.p. 187–188° C. |
| 292 | F | S | 0 | 5-methyl-1,2,4-oxadiazol-3-yl | m.p. 120–125° C. |
| 293 | H | O | 1 | pyridin-2-yl | |
| 294 | F | O | 1 | pyridin-2-yl | m.p. 127–128° C. (decomp.) |

TABLE 8

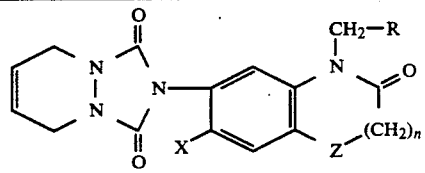

| Compound No. | X | Z | n | R | |
|---|---|---|---|---|---|
| 295 | H | O | 0 | 1,2-oxazol-3-yl | m.p. 214–215° C. |
| 296 | H | O | 1 | 1,2-oxazol-3-yl | m.p. 248–250° C. |
| 297 | H | O | 1 | 5-methyl-1,2,4-oxadiazol-3-yl | |
| 298 | F | O | 1 | 1,2-oxazol-3-yl | m.p. 248–251° C. |
| 299 | F | O | 1 | 5-methyl-1,2,4-oxadiazol-3-yl | m.p. 180–181° C. |
| 300 | F | S | 0 | 1,2-oxazol-3-yl | m.p. 140–143° C. |
| 301 | F | S | 0 | 5-methyl-1,2,4-oxadiazol-3-yl | m.p. 225–227° C. |
| 302 | H | O | 1 | pyridin-2-yl | |
| 303 | F | O | 1 | pyridin-2-yl | m.p. 167–169° C. |

TABLE 9

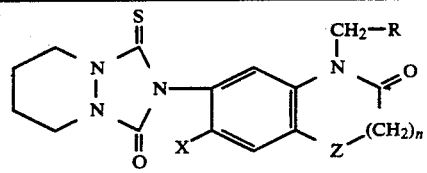

| Compound No. | X | Z | n | R | |
|---|---|---|---|---|---|
| 304 | F | O | 1 | 1,2-oxazol-3-yl | m.p. 225–227° C. |
| 305 | F | O | 1 | 5-methyl-1,2,4-oxadiazol-3-yl | m.p. 266–272° C. |
| 306 | F | S | 0 | 1,2-oxazol-3-yl | m.p. 254–256° C. |
| 307 | F | S | 0 | 5-methyl-1,2,4-oxadiazol-3-yl | m.p. 202–206° C. |

TABLE 9-continued

| Compound No. | X | Z | n | R | |
|---|---|---|---|---|---|
| 308 | H | O | 1 | pyridin-2-yl | |
| 309 | F | O | 1 | pyridin-2-yl | m.p. 163–168° C. |

TABLE 10

| Compound No. | X | Z | n | R | |
|---|---|---|---|---|---|
| 310 | H | O | 0 | 1,2-oxazol-3-yl | m.p. 178–179° C. |
| 311 | H | O | 1 | 1,2-oxazol-3-yl | m.p. 239–243° C. |
| 312 | H | O | 1 | 5-methyl-1,2,4-oxadiazol-3-yl | m.p. 221–222° C. |
| 313 | F | O | 1 | 1,2-oxazol-3-yl | m.p. 233–234° C. |
| 314 | F | O | 1 | 5-methyl-1,2,4-oxadiazol-3-yl | m.p. 227–228° C. |
| 315 | F | S | 0 | 1,2-oxazol-3-yl | m.p. 237–238° C. |
| 316 | F | S | 0 | 5-methyl-1,2,4-oxadiazol-3-yl | m.p. 251–255° C. |
| 317 | H | O | 1 | pyridin-2-yl | |
| 318 | F | O | 1 | pyridin-2-yl | m.p. 200–210° C. |

TABLE 11

| Compound No. | X | Z | n | R | |
|---|---|---|---|---|---|
| 319 | H | O | 1 | 1,2-oxazol-3-yl | |
| 320 | H | O | 1 | 5-methyl-1,2,4-oxadiazol-3-yl | |
| 321 | F | O | 1 | 1,2-oxazol-3-yl | |
| 322 | F | O | 1 | 5-methyl-1,2,4-oxadiazol-3-yl | |
| 323 | F | S | 0 | 1,2-oxazol-3-yl | |
| 324 | F | S | 0 | 5-methyl-1,2,4-oxadiazol-3-yl | amorphous |
| 325 | H | O | 1 | pyridin-2-yl | amorphous |
| 326 | F | O | 1 | pyridin-2-yl | m.p. 198–201° C. |

TABLE 12

| Compound No. | X | Z | n | R | |
|---|---|---|---|---|---|
| 327 | H | O | 1 | pyridin-2-yl | m.p. 218–222° C. |
| 328 | F | O | 1 | pyridin-2-yl | amorphous |
| 329 | F | S | 0 | 1,2-oxazol-3-yl | amorphous |
| 330 | F | O | 1 | 1,2-oxazol-3-yl | m.p. 186–192° C. |

TABLE 13

| Compound No. | X | Z | n | R | |
|---|---|---|---|---|---|
| 331 | H | O | 1 | pyridin-2-yl | m.p. 222–224° C. |
| 332 | F | O | 1 | pyridin-2-yl | |
| 333 | F | S | 0 | 1,2-oxazol-3-yl | m.p. 246–247° C. |
| 334 | F | S | 0 | 5-methyl-1,2,4-oxadiazol-3-yl | m.p. 225–227° C. |
| 335 | F | O | 1 | 1,2-oxadiazol-3-yl | m.p. 252–253° C. |

TABLE 14

| Compound No. | $R^4$—T | X | Z | n | R | |
|---|---|---|---|---|---|---|
| 336 | —OH | F | O | 1 | pyridin-2-yl | amorphous |
| 337 | Cl | F | O | 1 | pyridin-2-yl | (hydrochloride) amorphous |
| 338 | —OCCH$_3$ (O) | F | O | 1 | pyridin-2-yl | $n_D^{20}$ 1.5725 |
| 339 | —OCC$_2$H$_5$ (O) | F | O | 1 | pyridin-2-yl | |
| 340 | —OCH$_3$ | F | O | 1 | pyridin-2-yl | |
| 341 | —OC$_2$H$_5$ | F | O | 1 | pyridin-2-yl | amorphous |
| 342 | —SCH$_3$ | F | O | 1 | pyridin-2-yl | |
| 343 | —SC$_2$H$_5$ | F | O | 1 | pyridin-2-yl | |
| 344 | —N(CH$_3$)$_2$ | F | O | 1 | pyridin-2-yl | |

EXAMPLE 13

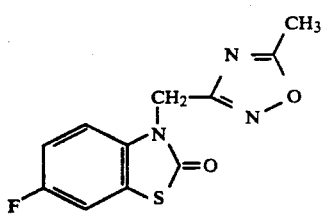

A mixture of 6-fluoro-2(3H)-benzothiazolone (8.45 g), acetonitrile (100 ml) and potassium carbonate (7.6 g) was prepared. To this mixture was added dropwise 3-chloromethyl-5-methyl-1,2,4-oxadiazole (7.3 g) at a temperature of 40° to 50° C. under stirring. The reaction mixture was heated under refluxing for 5 hours. The reaction mixture was then cooled and filtered. The filtrate was distilled under a reduced pressure, and the residue was admixed with ethyl acetate (200 ml) and water (100 ml). The resultant organic layer was separated and washed with a 5% aqueous potassium hydroxide solution, with water and then with a saturated aqueous sodium chloride solution, and dried over anhydrous sodium sulfate. The solvent was distilled off, and the residue was dissolved in a minimum amount of ethanol under heating. The solution thus formed was cooled to a temperature of 0° to 5° C. to precipitate a crystalline product, which was then separated by filtration, and dried, so that the aimed compound, i.e. 6-fluoro-3-(5-methyl-1,2,4-oxadiazol-3-ylmethyl)-2(3H)-benzothiazolone (12.1 g) was obtained. m.p. 142°–144° C.

EXAMPLE 14

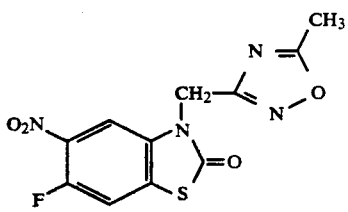

A compound of 6-fluoro-3-(5-methyl-1,2,4-oxadiazol-3-ylmethyl-2(3H)-benzothiazolone (11.5 g) was added portionwise to concentrated sulfuric acid (200 g) which had been cooled to a temperature of 5° to 10° C. The reaction mixture was stirred at a temperature of 0° to 5° C. for 10 minutes. To the reaction mixture was dropwise added a 98% nitric acid (3 g). The reaction mixture was stirred at a temperature of 0° to 5° C. for 2 hours, and then poured onto ice. Ethyl acetate (1 liter) was added to the the mixture, and the whole was stirred. The ethyl acetate layer was separated, washed with water, with a saturated aqueous sodium bicarbonate solution, and then with a saturated aqueous sodium chloride solution, and dried over anhydrous sodium sulfate. The solvent was distilled off, and the residue was recrystallized from ethanol, so that the aimed product, i.e. 6-fluoro-3-(5-methyl-1,2,4-oxadiazol-3-ylmethyl)-5-nitro-2(3H)-benzothiazolone (13.0 g) was obtained. m.p. 192°–193° C.

EXAMPLE 15

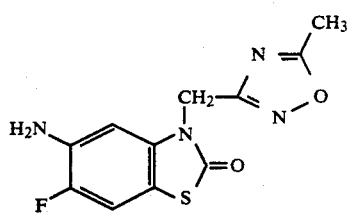

A mixture of 6-fluoro-3-(5-methyl-1,2,4-oxadiazol-3-ylmethyl)-5-nitro-2(3H)-benzothiazolone (3.1 g) and ethanol (40 ml) was prepared. To this mixture was dropwise added a solution of stannous chloride (3.3 mol equivalents per mol equivalent of the nitro compound) in concentrated hydrochloric acid (40 ml), at a temperature of 10° to 15° C. The reaction mixture was stirred at a temperature of 60° to 70° C. for 1.5 hours, and distilled under a reduced pressure to remove the ethanol and the hydrochloric acid therefrom. The resultant residue was admixed with ice (20 g). To the solution thus formed was added dropwise a 25% aqueous potassium hydroxide solution at a temperature of 10° to 15° C. to make the mixture alkaline. The mixture was extracted with dichloromethane (100 ml×2). The dichloromethane extract was washed with water, dried over anhydrous sodium sulfate, and evaporated under reduced pressure to obtain the aimed compound, i.e. 5-amino-6-fluoro-3-(5-methyl-1,2,4-oxadiazol-3-ylmethyl)-2(3H)-benzothiazolone (2.2 g). m.p. 158°–161° C.

It is also possible to prepare the above-mentioned compound by another manufacturing process, as shown below.

6-fluoro-2(3H)-benzothiazolone (82.9 g) was nitrated in conc. sulfuric acid (800 g) with a 98% nitric acid (5% excess of the theoretical amount) at a temperature of 0° to 5° C. under stirring for 1.5 hours. The reaction mixture was poured into ice water and filtered. The solid material separated by the filtration was dried, and recrystallized from acetone, so that 6-fluoro-5-nitro-2(3H)-benzothiazolone (67.7 g) was obtained. The purity of this compound was 92% (this purity was determined by HPLC). The whole amount of this compound was reduced with iron powder to obtain 5-amino-6-fluoro-2(3H)-benzothiazolone (52.4 g). 4 g of the amino compound were subjected to an alkylation operation with the aid of 3-chloromethyl-5-methyl-1,2,4-oxadiazole (2.9 g), in acetonitrile (100 ml) in the presence of potassium carbonate (3 g) as the dehydrochlorinating agent. This operation was carried out under reflux for 2 hours, so that the aimed compound, i.e. 5-amino-6-fluoro-3-(5-methyl-1,2,4-oxadiazol-3-ylmethyl)-2(3H)-benzothiazolone (5.3 g) was obtained. m.p. 156°–157° C.

EXAMPLE 16

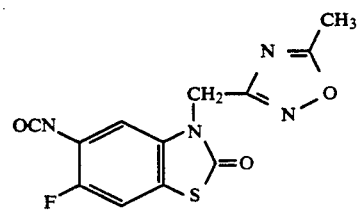

A mixture of 5-amino-6-fluoro-3-(5-methyl-1,2,4-oxadiazol-3-ylmethyl)-2(3H)-benzothiazolone (1.33 g) and dioxane (23 g) was prepared. To this mixture was dropwise added trichloromethyl chloroformate (1 g). The reaction mixture was heated under refluxing for 3 hours. The components with lower boiling points were distilled off, and the residue was dissolved in toluene (50 ml). The resulting solution was concentrated under a reduced pressure to dryness, so that the aimed compound, i.e. 6-fluoro-5-isocyanato-3-(5-methyl-1,2,4-oxadiazol-3-ylmethyl)-2(3H)-benzothiazolone (1.46 g) was obtained. m.p. 125°-127° C.

EXAMPLE 17

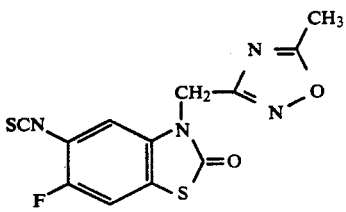

A mixture of 5-amino-6-fluoro-3-(5-methyl-1,2,4-oxadiazol-3-ylmethyl)-2(3H)-benzothiazolone (1.33 g), dichloromethane (10 ml) and ice (10 g) was prepared. To this mixture was added thiophosgene (0.7 g), and then portionwise added sodium bicarbonate at a temperature of 5° to 10° C. so as to make the mixture slightly alkaline. The mixture was stirred for 20 minutes, and tested to confirm whether the mixture was alkaline (if the mixture was acidic, then a further amount of sodium bicarbonate was added). The dichloromethane layer was separated, and the aqueous layer was extracted with fresh dichloromethane (10 ml×2). The dichloromethane layers were gathered together, washed with water, and distilled to remove the dichloromethane solvent therefrom. The resulting solid residue was recrystallized from a toluene-hexane solvent mixture, so that the aimed compound, i.e. 6-fluoro-5-isothiocyanato-3-(5-methyl-1,2,4-oxadiazol-3-ylmethyl)-2(3H)-benzothiazolone (1.49 g) was obtained. m.p. 168°-170° C.

EXAMPLE 18

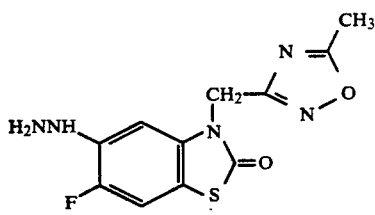

5-amino-6-fluoro-3-(5-methyl-1,2,4-oxadiazol-3-ylmethyl)-2(3H)-benzothiazolone (1.6 g) was added to a mixture of concentrated hydrochloric acid (5 ml) and water (5 ml). To the resultant solution was dropwise added an aqueous solution of nitrous acid (0.45 g) at a temperature of 0° to 5° C. The reaction mixture was stirred at a temperature of 0° to 5° C. for 30 minutes to complete the diazotization reaction.

The reaction mixture, which contained the diazotized product, was dropwise added at a temperature of 0° to 5° C. to a mixture of stannous chloride dihydrate (4.23 g) concentrated hydrochloric acid (6 ml). Then the reaction mixture was stirred at a temperature of 0° to 5° C. for 30 minutes. To the reaction mixture was dropwise added a 25% aqueous potassium hydroxide solution to make the mixture alkaline, and the mixture was extracted with dichloromethane (20 ml×2). The separated dichloromethane layer was washed with water, and dried over anhydrous sodium sulfate. The solvent was distilled off, so that the aimed compound, i.e. 6-fluoro-5-hydrazino-3-(5-methyl-1,2,4-oxadiazol-3-ylmethyl)-2(3H)-benzothiazolone (1.4 g) was obtained. m.p. 190°-192° C. (decomposition).

EXAMPLE 19

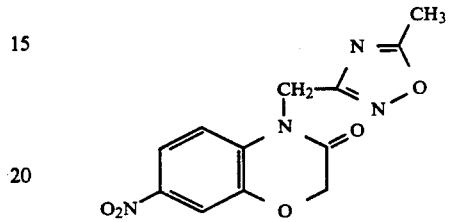

A mixture of 7-nitro-2H-1,4-benzoxazin-3(4H)-one (3.88 g) (this compound can be obtained by a process shown in J. Chem. Soc., 1928, p. 3046, or Synthesis, 1982, p. 986), potassium carbonate (3.1 g) and acetonitrile (80 ml) was prepared. To this mixture was dropwise added 3-chloromethyl-5-methyl-1,2,4-oxadiazole (2.92 g) at a temperature of 40° to 50° C. The reaction mixture was continuously stirred under refluxing for 4 hours, and then cooled. After that, the solvent was distilled off under a reduced pressure, and the residue was admixed with ethyl acetate (150 ml) and water (50 ml). The organic layer was separated, washed with a 5% aqueous potassium hydroxide solution, with water and then with a saturated aqueous sodium chloride solution, and dried over anhydrous sodium sulfate. The solvent was distilled off under a reduced pressure, and the residue thus obtained was recrystallized from toluene, so that the aimed compound, i.e. 4-(5-methyl-1,2,4-oxadiazol-3-ylmethyl)-7-nitro-2H-1,4-benzoxazin-3-(4H)-one (3.22 g) was obtained. m.p. 182°-183° C.

EXAMPLE 20

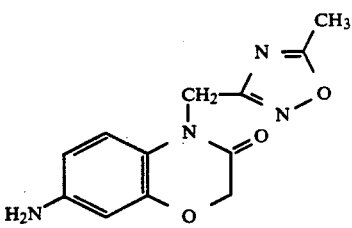

A mixture of 4-(5-methyl-1,2,4-oxadiazol-3-ylmethyl)-7-nitro-2H-1,4-benzoxazin-3(4H)-one (3.2 g) and ethanol (40 ml) was prepared. To this mixture was added a solution of stannous chloride dihydrate (11.3 g) in concentrated hydrochloric acid (44 ml) at a temperature of 10° to 20° C. The reaction mixture was stirred at a temperature of 60° to 70° C., and distilled to dryness under a reduced pressure. The resulting residue was admixed with ice (150 g). To the mixture thus obtained was added dropwise a 25% aqueous potassium hydroxide solution at a temperature of 0° to 10° C. to render the mixture alkaline. The resultant alkaline solution was extracted with dichloromethane (80 ml×2). The dichloromethane layer was washed with water, and dried over anhydrous sodium sulfate. The dichloromethane solvent was distilled off under a reduced pressure, and the resultant solid residue (1.3 g) was recrystallized from toluene, so that the aimed compound, i.e. 7-amino-4-(5-methyl-1,2,4-oxadiazol-3-ylmethyl)-2H-1,4-benzoxazin-3(4H)-one (1.1 g) was obtained. m.p. 146°-147.5° C.

EXAMPLE 21

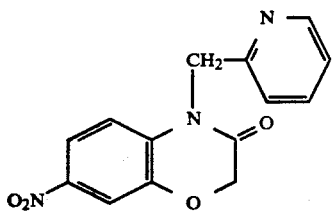

A mixture of 7-nitro-2H-1,4-benzoxazin-3(4H)-one (1.94 g), potassium carbonate (15.18 g) and acetonitrile (200 ml) was stirred at 60° C. for 30 minutes, cooled to a temperature of 20° to 30° C., and supplied dropwise with 2-(chloromethyl)pyridine (14 g). The reaction mixture was heated to a temperature of 60° to 65° C. for 30 minutes, then heated under reflux for 3 hours, cooled to a temperature of 20° to 30° C., and filtered.

The resultant filtrate was distilled under a reduced pressure to remove the substances having lower boiling points therefrom. The resulting residue was dissolved in dichloromethane (200 ml), and washed with a 5% aqueous potassium hydroxide solution and then with water, and dried over anhydrous sodium sulfate. The dichloromethane was distilled off, the residue thus obtained was recrystallized from ethanol, so that the aimed compound i.e. 7-nitro-4-(pyridin-2-ylmethyl)-2H-1,4-benzoxazin-3(4H)-one (23.1 g) was obtained. m.p. 175°-176° C.

EXAMPLE 22

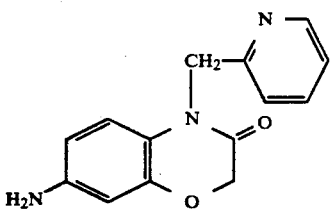

A mixture of iron powder (19 g), water (100 ml), acetic acid (5.7 g) and ethanol (50 ml) was stirred at a temperature of 70° to 80° C. To this mixture was portionwise added the compound of Example 9 (16 g). The reaction mixture was further supplied with ethanol (50 ml) and refluxed for 1 hour. A considerable amount of the ethanol was distilled off under atmospheric pressure. Then the reaction mixture was admixed with dichloromethane (200 ml), and stirred sufficiently, cooled to a temperature of 10° to 20° C. Thereafter, the reaction mixture was filtered with the aid of Celite, and the filter cake was washed with dichloromethane (50 ml×2). The organic layer was separated from the filtrate and from the wash liquid, washed with a saturated aqueous sodium bicarbonate solution, and dried over anhydrous sodium sulfate. The solvent was distilled off, and the residue was recrystallized from a toluene-hexane (3:1) solvent mixture, so that the aimed compound i.e. 7-amino-4-(pyridin-2-ylmethyl)-2H-1,4-benzoxazin-3(4H)-one (12 g) was obtained. m.p. 140°-141° C.

EXAMPLE 23

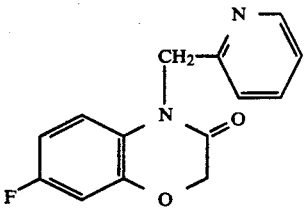

The compound (4.13 g) of Example 22 was dissolved in a mixture of concentrated hydrochloric acid (5 g) and water (1.2 g). To the resulting solution was portionwise added sodium nitrite (1.2 g). at a temperature of 0° to 5° C. The reaction mixture was stirred at 0° to 5° C. for 30 minutes, and supplied dropwise with 42% hydrofluoroboric acid (7 g), stirred at 0° to 5° C. for 30 minutes, further stirred at 20° to 30° C. for 2 hours, and again cooled to a temperature of 0° to 5° C. The crystalline product thus formed was separated by filtration, and washed in ice water (20 ml), and dried in air.

The dried solid product (5.5 g) thus obtained was suspended in dichlorobenzene (50 ml), and this suspension was heated under reflux for 30 minutes. The dichlorobenzene and the substances having lower boiling point were distilled off under a reduced pressure, and the resultant residue was admixed with a 5% aqueous potassium hydroxide solution (200 ml). The mixture thus formed was stirred at a temperature of 20° to 30° C. for 1 hour, admixed with ethyl acetate (200 ml) to effect an extraction operation. The ethyl acetate extract was dried over anhydrous sodium sulfate. The solvent was distilled off, and the residue thus formed was extracted with hot hexane. The hexane extract was cooled to a temperature of 5° to 10° C., and the resulting crystalline product was separated by filtration, so that the aimed compound i.e. 7-fluoro-4-(pyridin-2-ylmethyl)-2H-1,4-benzoxazin-3(4H)-one (1.9 g) was obtained. m.p. 82°-84° C.

EXAMPLE 24

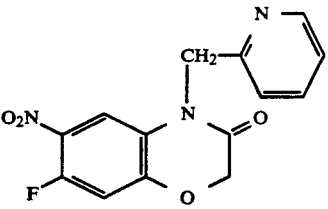

The compound (8.96 g) of Example 23 was added portionwise to concentrated sulfuric acid (100 g) which had been cooled to a temperature of 0° to 5° C. The resultant solution was stirred for 10 minutes and supplied dropwise with a 98% nitric acid (2.34 g) at a temperature of 0° to 5° C. The reaction mixture was stirred at a temperature of 5° to 10° C. for 1 hour, and poured into ice (300 g). Then the reaction mixture was neutralized with sodium bicarbonate, and extracted with ethyl acetate (250 ml). The organic layer was separated, washed with water, and dried over anhydrous sodium sulfate. The solvent was distilled off, the residue was recrystallized from ethanol, so that the aimed compound i.e. 7-fluoro-6-nitro-4-(pyridin-2-ylmethyl)-2H-1,4-benzoxazin-3(4H)-one (5.8 g) was obtained. m.p. 129°–130° C.

EXAMPLE 25

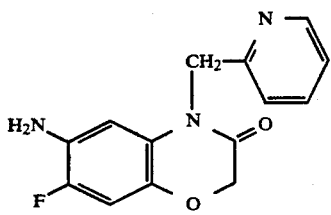

The compound (12.56 g) of Example 24 was reduced according to a method similar to that shown in Example 22, with the aid of iron powder (13.3 g), water (80 ml), acetic acid (4 g) and ethanol (100 ml). The aimed compound i.e. 6-amino-7-fluoro-4-(pyridin-2-ylmethyl)-2H-1,4-benzoxazin-3(4H)-one (10.4 g) was obtained. m.p. 149°–152° C.

EXAMPLE 26

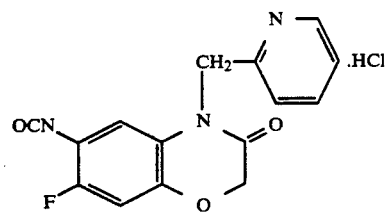

The compound (5 g) of Example 25 was dissolved in dioxane (60 ml). To this solution was dropwise added trichloromethyl chloroformate (4 g) at a temperature of 10° to 20° C. The reaction mixture was heated under reflux and under stirring for 5 hours, and then cooled to a temperature of 20° to 25° C. The solid portion was separated by filtration, and washed with toluene (10 ml×2), so that the aimed compound i.e. 7-fluoro-6-isocyanato-4-(pyridin-2-ylmethyl)-2H-1,4-benzoxazin-3(4H)-one hydrochloride (6.1 g) was obtained. m.p. 300°–305° C.

EXAMPLE 27

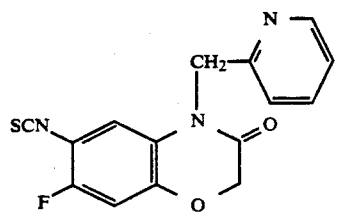

A mixture of the compound (2.73 g) of Example 25, dichloromethane (30 ml) and water (25 ml) was cooled to a temperature of 5° to 15° C. To this mixture was dropwise added thiophosgene (1.3 g). Thereafter, sodium bicarbonate was portionwise added to the reaction mixture until the reaction mixture had shown a slight alkalinity. The reaction mixture was stirred at a temperature of 10° to 20° C. for 30 minutes. The organic layer was separated, and dried over anhydrous sodium sulfate. The solvent was distilled off, and the residue was recrystallized from a toluene/n-hexane mixture, so that the aimed compound i.e. 7-fluoro-6-isothiocyanato-4-(pyridin-2-ylmethyl)-2H-1,4-benzoxazin-3(4H)-one (2.3 g) was obtained. m.p. 106°–109° C.

EXAMPLE 28

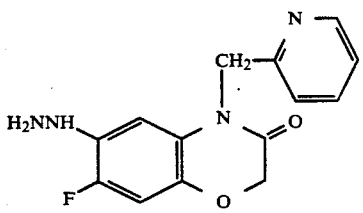

A mixture of the compound (5.46 g) of Example 25, concentrated hydrochloric acid (10 ml) and water (10 ml) was prepared. To this mixture was portionwise added sodium nitrite (1.4 g) at a temperature of 0° to 5° C. The mixture was stirred at a temperature of 0° to 5° C. for 30 minutes.

The resultant diazotized liquid was dropwise added to a solution comprising stannous chloride dihydrate (14 g) and concentrated hydrochloric acid (14 ml).

The reaction mixture was stirred at a temperature of 0° to 5° C. for 30 minutes, and supplied dropwise with a 40% aqueous postassium hydroxide solution at a temperature lower than 10° C., so that the reaction mixture became alkaline. The reaction mixture was admixed with dichloromethane (200 ml), stirred for several minutes, and filtered. The separated dichloromethane layer was washed with water and dried over anhydrous sodium sulfate. The solvent was distilled off, and the residue was recrystallized from ethanol, so that the aimed compound i.e. 7-fluoro-6-hydrazino-4-(pyridin-2-ylmethyl)-2H-1,4-benzoxazin-3(4H)-one (3.5 g) was obtained. m.p. 150°–154° C.

According to the same method as in the above Examples 13 to 28, the intermediates for the compounds of the formula (I) can be obtained as shown in the following Table 15 together with the intermediates obtained in Examples 13 to 28.

TABLE 15

| Intermediate | E | X | Z | n | R | m.p., °C. |
|---|---|---|---|---|---|---|
| 1 | —NH₂ | H | O | 0 | cyclopropyl | |
| 2 | —NH₂ | F | O | 0 | cyclopropyl | |
| 3 | —NH₂ | F | S | 0 | cyclopropyl | |
| 4 | —NCO | F | S | 0 | cyclopropyl | |
| 5 | —NCS | F | S | 0 | cyclopropyl | |
| 6 | —NH₂ | H | O | 1 | cyclopropyl | |
| 7 | H | H₂N | O | 1 | cyclopropyl | 127–129 |
| 8 | H | F | O | 1 | cyclopropyl | 55–56 |
| 9 | —NO₂ | F | O | 1 | cyclopropyl | |
| 10 | —NH₂ | F | O | 1 | cyclopropyl | |
| 11 | —NCO | F | O | 1 | cyclopropyl | |
| 12 | —NCS | F | O | 1 | cyclopropyl | |
| 13 | —NH₂ | H | O | 0 | isoxazol-3-yl | 127–130 |
| 14 | —NCO | H | O | 0 | isoxazol-3-yl | 96–101 |
| 15 | —NCS | H | O | 0 | isoxazol-3-yl | |
| 16 | —NH₂ | F | O | 0 | isoxazol-3-yl | 166–171 |
| 17 | —NCO | F | O | 0 | isoxazol-3-yl | |
| 18 | —NCS | F | O | 0 | isoxazol-3-yl | |
| 19 | H | F | S | 0 | isoxazol-3-yl | 94–97 |
| 20 | —NO₂ | F | S | 0 | isoxazol-3-yl | 166–168 |
| 21 | —NH₂ | F | S | 0 | isoxazol-3-yl | 164–166 |
| 22 | —NCO | F | S | 0 | isoxazol-3-yl | 188–189 |
| 23 | —NCS | F | S | 0 | isoxazol-3-yl | 157–162 |
| 24 | —NH₂ | H | O | 1 | isoxazol-3-yl | 130–132 |
| 25 | —NCO | H | O | 1 | isoxazol-3-yl | oil |
| 26 | —NCS | H | O | 1 | isoxazol-3-yl | |
| 27 | H | F | O | 1 | isoxazol-3-yl | 109.5–110.5 |
| 28 | —NO₂ | F | O | 1 | isoxazol-3-yl | 153–155 |
| 29 | —NH₂ | F | O | 1 | isoxazol-3-yl | 187–188 |
| 30 | —NCO | F | O | 1 | isoxazol-3-yl | 111–113 |
| 31 | —NCS | F | O | 1 | isoxazol-3-yl | 125–126 |
| 32 | —NH₂ | H | O | 0 | 5-methyl-1,2,4-oxadiazol-3-yl | |
| 33 | —NH₂ | F | O | 0 | 5-methyl-1,2,4-oxadiazol-3-yl | |
| 34 | H | F | S | 0 | 5-methyl-1,2,4-oxadiazol-3-yl | 142–144 |
| 35 | —NO₂ | F | S | 0 | 5-methyl-1,2,4-oxadiazol-3-yl | 192–193 |
| 36 | —NH₂ | F | S | 0 | 5-methyl-1,2,4-oxadiazol-3-yl | 156–157 |
| 37 | —NCO | F | S | 0 | 5-methyl-1,2,4-oxadiazol-3-yl | 125–127 |
| 38 | —NCS | F | S | 0 | 5-methyl-1,2,4-oxadiazol-3-yl | 168–170 |
| 39 | —NHNH₂ | F | S | 0 | 5-methyl-1,2,4-oxadiazol-3-yl | 190–192 (decomp.) |
| 40 | —NH₂ | H | O | 1 | 5-methyl-1,2,4-oxadiazol-3-yl | 178–181 |
| 41 | —NCO | H | O | 1 | 5-methyl-1,2,4-oxadiazol-3-yl | |
| 42 | —NCS | H | O | 1 | 5-methyl-1,2,4-oxadiazol-3-yl | |
| 43 | —NH₂ | F | O | 1 | 5-methyl-1,2,4-oxadiazol-3-yl | 154–157 |
| 44 | —NCO | F | O | 1 | 5-methyl-1,2,4-oxadiazol-3-yl | oil |
| 45 | —NCS | F | O | 1 | 5-methyl-1,2,4-oxadiazol-3-yl | 110–110 |
| 46 | —NH₂ | H | O | 0 | 3-methyl-1,2,4-oxadiazol-5-yl | |
| 47 | —NH₂ | F | O | 0 | 3-methyl-1,2,4-oxadiazol-5-yl | |
| 48 | H | F | S | 0 | 3-methyl-1,2,4-oxadiazol-5-yl | 103–105 |
| 49 | —NO₂ | F | S | 0 | 3-methyl-1,2,4-oxadiazol-5-yl | 145–146 |
| 50 | —NH₂ | F | S | 0 | 3-methyl-1,2,4-oxadiazol-5-yl | |
| 51 | —NH₂ | H | O | 1 | 3-methyl-1,2,4-oxadiazol-5-yl | |
| 52 | —NH₂ | F | O | 1 | 3-methyl-1,2,4-oxadiazol-5-yl | |

TABLE 15-continued

Structure: benzene ring with E and X substituents, and N(CH$_2$-R)-C(=O)-(CH$_2$)$_n$-Z- connected to the ring.

| Intermediate | E | X | Z | n | R | m.p., °C. |
|---|---|---|---|---|---|---|
| 53 | —NH$_2$ | H | O | 0 | 3-methyl-1,2,5-oxadiazol-5-yl | |
| 54 | —NH$_2$ | F | O | 0 | 3-methyl-1,2,5-oxadiazol-5-yl | |
| 55 | H | F | S | 0 | 3-methyl-1,2,5-oxadiazol-5-yl | |
| 56 | —NO$_2$ | F | S | 0 | 3-methyl-1,2,5-oxadiazol-5-yl | |
| 57 | —NH$_2$ | F | S | 0 | 3-methyl-1,2,5-oxadiazol-5-yl | |
| 58 | —NCO | F | S | 0 | 3-methyl-1,2,5-oxadiazol-5-yl | |
| 59 | —NCS | F | S | 0 | 3-methyl-1,2,5-oxadiazol-5-yl | |
| 60 | —NH$_2$ | H | O | 1 | 3-methyl-1,2,5-oxadiazol-5-yl | |
| 61 | —NH$_2$ | F | O | 1 | 3-methyl-1,2,5-oxadiazol-5-yl | |
| 62 | —NH$_2$ | F | O | 0 | thiazol-4-yl | |
| 63 | —NH$_2$ | F | S | 0 | thiazol-4-yl | 147–149 |
| 64 | —NH$_2$ | H | O | 1 | thiazol-4-yl | |
| 65 | —NH$_2$ | F | O | 1 | thiazol-4-yl | |
| 66 | —NH$_2$ | F | O | 0 | 1,2,5-thiadiazol-3-yl | |
| 67 | —NH$_2$ | F | S | 0 | 1,2,5-thiadiazol-3-yl | |
| 68 | —NH$_2$ | H | O | 1 | 1,2,5-thiadiazol-3-yl | |
| 69 | —NH$_2$ | F | O | 1 | 1,2,5-thiadiazol-3-yl | |
| 70 | —NH$_2$ | F | O | 0 | 5-methoxy-1,2,4-thiadiazol-3-yl | |
| 71 | —NH$_2$ | F | S | 0 | 5-methoxy-1,2,4-thiadiazol-3-yl | |
| 72 | —NH$_2$ | H | O | 1 | 5-methoxy-1,2,4-thiadiazol-3-yl | |
| 73 | —NH$_2$ | F | O | 1 | 5-methoxy-1,2,4-thiadiazol-3-yl | |
| 74 | —NH$_2$ | H | O | 0 | pyridin-2-yl | |
| 75 | —NH$_2$ | F | O | 0 | pyridin-2-yl | |
| 76 | H | F | S | 0 | pyridin-2-yl | 121–122.5 |
| 77 | —NO$_2$ | F | S | 0 | pyridin-2-yl | 166–171 |
| 78 | —NH$_2$ | F | S | 0 | pyridin-2-yl | 129–132 |
| 79 | —NCO | F | S | 0 | pyridin-2-yl | |
| 80 | —NCS | F | S | 0 | pyridin-2-yl | |
| 81 | —NO$_2$ | H | O | 1 | pyridin-2-yl | 141–143 |
| 82 | —NH$_2$ | H | O | 1 | pyridin-2-yl | 146–148 |
| 83 | —NCO | H | O | 1 | pyridin-2-yl | (hydrochloride) |
| 84 | —NCS | H | O | 1 | pyridin-2-yl | 118–120 |
| 85 | —NHNH$_2$ | H | O | 1 | pyridin-2-yl | 100–108 |
| 86 | H | F | O | 1 | pyridin-2-yl | 77–78 |
| 87 | —NO$_2$ | F | O | 1 | pyridin-2-yl | 129–130 |
| 88 | —NH$_2$ | F | O | 1 | pyridin-2-yl | 150–151 |
| 89 | —NCO | F | O | 1 | pyridin-2-yl | 300–305 (hydrochloride) |
| 90 | —NCS | F | O | 1 | pyridin-2-yl | 106–109 |
| 91 | —NHNH$_2$ | F | O | 1 | pyridin-2-yl | 150–154 |
| 92 | —NH$_2$ | H | O | 0 | pyrazin-2-yl | |
| 93 | —NH$_2$ | F | O | 0 | pyrazin-2-yl | |
| 94 | —NH$_2$ | F | S | 0 | pyrazin-2-yl | |
| 95 | —NCO | F | S | 0 | pyrazin-2-yl | |
| 96 | —NCS | F | S | 0 | pyrazin-2-yl | |
| 97 | —NH$_2$ | H | O | 1 | pyrazin-2-yl | |
| 98 | —NH$_2$ | F | O | 1 | pyrazin-2-yl | 175–178 |

USE EXAMPLES

Comparison Substances

E-1: (a disclosure in EP-OS 170191/Compound No. 2)

E-2: (a disclosure in EP-OS 170191/compound No.10)

EXAMPLE 29

Test on weeds in a flooded paddy by water surface application

Preparation of an active compound formulation

Carrier: 5 parts by weight of acetone
Emulsifier: 1 part by weight of benzyloxy polyglycol ether A formulation of an active compound was obtained as an emulsifiable concentrate by mixing 1 part by weight of the active compound with the above-mentioned amounts of the carrier and the emulsifying agent. A predetermined amount of the formulation was diluted with water.

Testing method

Paddy soil was filled in pots (1/2,000 are; 25×20×9 cm), and rice seedlings (variety: "Nihonbare") in the 2.5-leaf stage (15 cm tall) were transplanted at two places per pot each as a stock of three seedlings. Seeds of barnyard grass (*Echinochloa oryzicola* Vasing.), umbrella plant (*Cyperus difformis* L.), monochoria (*Monochoria vaginalis*, and annual broadleaved weeds false pimpernel (*Lindernia pyxidaria* L.), *Rotala indica*, American waterwort (*Elatine triandra*), red stem (*Ammannia multiflora* Roxburgh) and *Dopatrium junceum* Hamilton were sown and the pots were maintained wet. Two days later, the pots were flooded to a depth of about 2 to 3 cm. Five days after the transplantation of the seedlings, the compound of this invention, in the form of an emulsifiable concentrate as prepared above, was applied to the water surface by a pipette in a predetermined amount. Thereafter, the flooded condition of about 3 cm was maintained, and four weeks after the chemical treatment, the herbicidal effect and the phytotoxicity to rice were evaluated and rated on the scale of 0 to 5 as follows:

Herbicidal effect (evaluated by a weed killing ratio based on a non-treated lot):
5: at least 95% (withered)
4: at least 80% but less than 95%
3: at least 50% but less than 80%
2: at least 30% but less than 50%
1: at least 10% but less than 30%
0: less than 10% (no effect), Phytotoxicity to crop (evaluated based on a non-treated lot):
5: at least 90% (fatal injury)
4: at least 50% but less than 90%
3: at least 30% but less than 50%
2: at least 10% but less than 30%
1: more than 0 but less than 10%
0: 0% (no phytotoxicity), The test results are shown in Table 16

TABLE 16

| Active compound | Amount of active compound (kg/ha) | Barnyard grass | Umbrella plant | Monochoria | Broadleaved grass | Phytotoxicity to rice |
|---|---|---|---|---|---|---|
| No. 146 | 0.25 | 4 | 5 | 5 | 5 | 0 |
|  | 0.125 | 3 | 5 | 4 | 5 | 0 |
| No. 159 | 0.25 | 5 | 5 | 5 | 5 | 2 |
|  | 0.125 | 5 | 5 | 5 | 5 | 1 |
|  | 0.06 | 5 | 5 | 5 | 5 | 0 |
| No. 183 | 0.25 | 5 | 5 | 5 | 5 | 1 |
|  | 0.125 | 4 | 5 | 5 | 5 | 0 |
|  | 0.06 | 4 | 5 | 4 | 5 | 0 |
| No. 197 | 0.25 | 5 | 5 | 5 | 5 | 1 |
|  | 0.125 | 4 | 5 | 5 | 5 | 0 |
| No. 249 | 0.25 | 4 | 5 | 5 | 5 | 0 |
|  | 0.125 | 3 | 4 | 4 | 5 | 0 |
| No. 257 | 0.25 | 4 | 5 | 5 | 5 | 0 |
|  | 0.125 | 4 | 5 | 4 | 5 | 0 |
| No. 284 | 0.25 | 5 | 5 | 5 | 5 | 0 |
|  | 0.125 | 4 | 5 | 5 | 5 | 0 |
| Comparison |  |  |  |  |  |  |
| E-1 | 0.5 | 5 | 5 | 5 | 5 | 4 |
|  | 0.25 | 4 | 5 | 3 | 4 | 3 |
|  | 0.125 | 2 | 5 | 3 | 4 | 2 |
| E-2 | 0.25 | 3 | 5 | 4 | 4 | 3 |
|  | 0.125 | 1 | 3 | 2 | 2 | 2 |

EXAMPLE 30

Test on upland weeds by soil treatment before emergence

In a greenhouse; soy bean seeds were sown in 500 $cm^2$ pots filled with upland farm soil, and soil containing seeds of barnyard grass (*Echinochloa crus-galli*), livid amaranth (*Amaranthus lividus* L.) and goosefoot (*Chenopodium album* L.) was put over the soil in the pots in a depth of 1 cm.

One day after the sowing, a test chemical in a predetermined concentration, prepared as in Example 29, was uniformly sprayed over the surface layer of the soil in each of the test pots.

Four weeks after the spraying, the herbicidal effect and the phytotoxicity to crops were examined on the same standards as in Example 29.

The test results are shown in Table 17.

TABLE 17

| Active compound | Amount of active compound (kg/ha) | Barnyard grass | Livid amaranth | Goosefoot | Phytotoxic effect on soy bean plants |
|---|---|---|---|---|---|
| No. 146 | 0.25 | 4 | 5 | 5 | 0 |
|  | 0.125 | 3 | 5 | 5 | 0 |
| No. 159 | 0.25 | 5 | 5 | 5 | 1 |
|  | 0.125 | 5 | 5 | 5 | 0 |
|  | 0.06 | 4 | 5 | 5 | 0 |
| No. 183 | 0.25 | 4 | 5 | 5 | 0 |
|  | 0.125 | 3 | 5 | 5 | 0 |
| No. 248 | 0.25 | 4 | 5 | 5 | 1 |
|  | 0.125 | 3 | 5 | 5 | 0 |
| No. 257 | 0.25 | 5 | 5 | 5 | 0 |
|  | 0.125 | 3 | 5 | 5 | 0 |

TABLE 17-continued

| Active compound | Amount of active compound (kg/ha) | Herbicidal effect on weeds | | | Phytotoxic effect on soy bean plants |
|---|---|---|---|---|---|
| | | Barnyard grass | Livid amaranth | Goose-foot | |
| Comparison | | | | | |
| E-1 | 0.5 | 4 | 5 | 5 | 4 |
| | 0.25 | 3 | 5 | 5 | 3 |
| | 0.125 | 3 | 5 | 3 | 2 |
| E-2 | 0.5 | 4 | 5 | 5 | 4 |
| | 0.25 | 3 | 5 | 5 | 3 |

EXAMPLE 31

Test on upland farm weeds by foliar treatment

In a greenhouse, wheat seeds and corn seeds were sown in 500 cm² pots filled with upland farm soil, and soil containing seeds of Digitaria (*Digitaria sanguinalis*), livid amaranth (*Amaranthus lividus* L.) and goosefoot (*Chenopodium album* L.) was put over the soil in the pots in a depth of 1 cm.

After sowing, the plants were grown for 14 days and a test chemical in a predetermined concentration, prepared as in Example 29, was uniformly sprayed over the test plants in each of the test pots.

Four weeks after the spraying, the herbicidal effect and the phytotoxicity to crops were examined on the same standards as in Example 29. The results are shown in Table 18.

TABLE 18

| Active compound | Amount of active compounds (kg/ha) | Herbicidal effect on weeds | | | Phytotoxicity | |
|---|---|---|---|---|---|---|
| | | Digitaria | Livid amaranth | Goose-foot | wheat | corn |
| No. 146 | 0.25 | 4 | 5 | 5 | 0 | 0 |
| | 0.125 | 3 | 5 | 5 | 0 | 0 |
| No. 159 | 0.25 | 5 | 5 | 5 | 1 | 1 |
| | 0.125 | 5 | 5 | 5 | 0 | 0 |
| | 0.06 | 4 | 5 | 5 | 0 | 0 |
| No. 197 | 0.25 | 4 | 5 | 5 | 1 | 1 |
| | 0.125 | 3 | 5 | 5 | 0 | 0 |
| No. 257 | 0.25 | 4 | 5 | 5 | 1 | 1 |
| | 0.125 | 4 | 5 | 5 | 0 | 0 |
| No. 284 | 0.25 | 4 | 5 | 5 | 0 | 0 |
| | 0.125 | 3 | 5 | 5 | 0 | 0 |
| Comparison | | | | | | |
| E-1 | 0.5 | 5 | 5 | 5 | 4 | 4 |
| | 0.25 | 5 | 5 | 5 | 2 | 3 |
| | 0.125 | 4 | 5 | 5 | 1 | 1 |
| E-2 | 0.25 | 4 | 5 | 5 | 3 | 4 |
| | 0.125 | 3 | 5 | 5 | 2 | 3 |

It will be appreciated that the instant specification and claims are set forth by way of illustration and not limitation, and that various modifications and changes may be made without departing from the spirit and scope of the present invention.

We claim:

1. A benzo-fused cyclic compound of the formula

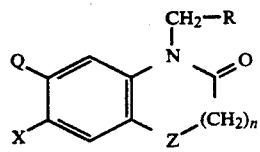

(I)

wherein Q is

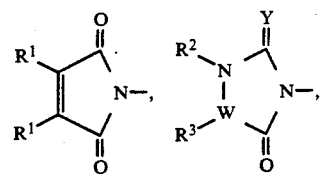

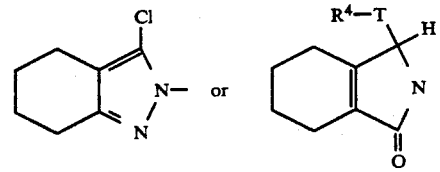

in which
R¹ is methyl or both R's together form tetramethylene,
R² and R³ together represent tetramethylene or $-CH_2CH=CHCH_2-$,
R⁴ is hydrogen, $C_1-C_4$-alkyl, $C_1-C_4$-alkylcarbonyl, or phenyl,
Y is O or S,
W is

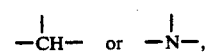

T is O, S, —NH— or,

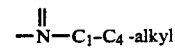

or
R⁴—T— may represent chlorine,
Z is O or S,
X is hydrogen or halogen,
n is 0 or 1 and
R is $C_{3-6}$ cycloalkyl, an optionally substituted heterocyclic group selected from the group consisting of tetrahydrofuran, furan, thiophene, pyrazole, imidazole, 1,2,4-triazole, tetrazole, isoxazole, oxazole, 1,2,4-oxadiazole, 1,2,5-oxadiazole, 1,3,4-oxadiazole, isothiazole, thiazole, 1,2,3-thiadiazole, 1,2,4-thiadiazole, 1,2,5-thiadiazole, 1,3,4-thiadiazole, pyridine, pyrimidine and pyrazine, but other than pyridyl if n is 0, the optional substituents being independently selected from the group consisting of amino, methylamino, ethylamino, dimethylamino, formylamino, acetamido, fluoro, chloro, bromo, methoxy, ethoxy, methylthio, ethylthio, methyl, ethyl, isopropyl, trichloromethyl, trifluoromethyl and methoxymethyl,
or a salt thereof.

2. A compound according to claim 1, in which Q is

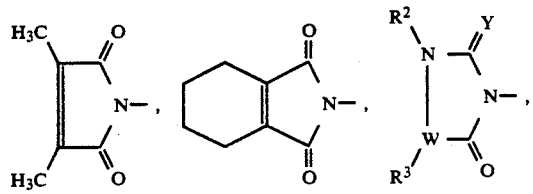

-continued
or

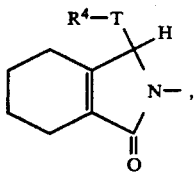

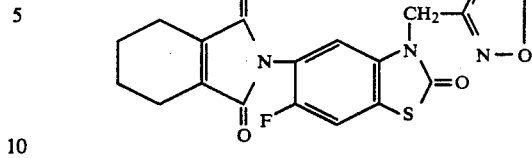

in which

R² represents tetramethylene or —CH₂CH=CHCH₂— together with R³,

R⁴ is hydrogen, methyl, ethyl, methylcarbonyl or phenyl,

T is O or S, or R⁴—T— may represent chlorine,

X is hydrogen or flourine, and

R is cyclopropyl, or an optionally substituted heterocyclic group selected from the group consisting of tetrahydrofuran, furan, thiophene, pyrazole, imidazole, 1,2,4-triazole, tetrazole, isoxazole, oxazole, 1,2,4-oxadiazole, 1,2,5-oxadiazole, 1,3,4-oxadiazole, isothiazole, thiazole, 1,2,3-thiadiazole, 1,2,4-thiadiazole, 1,2,5-thiadiazole, 1,3,4-thiadiazole, pyridine, pyrimidine and pyrazine, but other than pyridyl if n is O, the optional substituents being independently selected from the group consisting of amino, methylamino, ethylamino, dimethylamino, formylamino, acetamido, fluoro, chloro, bromo, methoxy, ethoxy, methylthio, ethylthio, methyl, ethyl, isopropyl, trichloromethyl, trifluoromethyl and/or methoxymethyl.

3. A compound according to claim 1, in which Q is

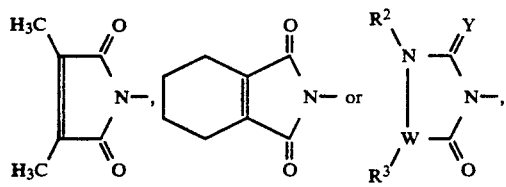

X is fluorine;

4. A compound according to claim 1, wherein such compound is 6-fluoro-3-(3-methyl-1,2,5-oxadiazol-4-ylmethyl)-5-(4,5,6,7-tetrahydro-2H-isoindole-1,3-dion-2-yl)-2(3H)-benzthiazolone of the formula or a salt thereof.

5. A herbicidal composition comprising a herbicidally effective amount of a compound or salt according to claim 1 and a diluent.

6. A method of combating unwanted vegetation which comprises applying to such vegetation or to a locus from which it is desired to exclude such vegetation a herbicidally effective amount of a compound or salt according to claim 1.

7. The method according to claim 6, wherein such compound is
6-fluoro-3-(3-methyl-1,2,5-oxadiazol-4-ylmethyl)-5-(4,5,6,7-tetrahydro-2H-isoindole-1,3-dion-2-yl)-2(3H)-benzthiazolone,
or a salt thereof.

8. A compound of the formula

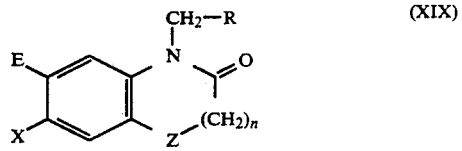

(XIX)

wherein

E is hydrogen, nitro, amino, hydrazino, cyanato or thiocyanato.

X is hydrogen or halogen,

Z is O or S,

R is $C_{3-6}$ cycloalkyl, an optionally substituted heterocyclic group selected from the group consisting of tetrahydrofuran, furan, thiophene, pyrazole, imidazole, 1,2,4-triazole, tetrazole, isoxazole, oxazole, 1,2,4-oxadiazole, 1,2,5-oxadiazole, 1,3,4-oxadiazole, isothiazole, thiazole, 1,2,3-thiadiazole, 1,2,4-thiadiazole, 1,2,5-thiadiazole, 1,3,4-thiadiazole, pyridine, pyrimidine and pyrazine, the optional substituents being independently selected from the group consisting of amino, methylamino, ethylamino, dimenthylamino, formylamino, acetamido, fluoro, chloro, bromo, methoxy, ethoxy, methylthio, ethylthio, methyl, ethyl, isopropyl, trichloromethyl, trifluoromethyl and methoxymethyl, and n is 0 or 1.

* * * * *

UNITED STATES PATENT AND TRADEMARK OFFICE
CERTIFICATE OF CORRECTION

PATENT NO. : 5,077,401

DATED : December 31, 1991

INVENTOR(S) : Kume et al.

It is certified that error appears in the above-identified patent and that said Letters Patent is hereby corrected as shown below:

Col. 55, claim 3   Before " X " insert -- and --, after " fluorine "
lines 2-3          delete " ; " and substitute -- . --

Signed and Sealed this

Fifth Day of October, 1993

*Attest:*

BRUCE LEHMAN

*Attesting Officer*    *Commissioner of Patents and Trademarks*